US007973029B2

(12) United States Patent
Montgomery et al.

(10) Patent No.: US 7,973,029 B2
(45) Date of Patent: Jul. 5, 2011

(54) INHALED AZTREONAM LYSINE FOR THE TREATMENT OF DEFICITS IN HEALTH-RELATED QUALITY-OF-LIFE IN LUNG DISEASES

(75) Inventors: Alan B. Montgomery, Medina, WA (US); Melissa A. Yeager, Woodville, WA (US)

(73) Assignee: Gilead Sciences, Inc., Foster City, CA (US)

( * ) Notice: Subject to any disclaimer, the term of this patent is extended or adjusted under 35 U.S.C. 154(b) by 203 days.

(21) Appl. No.: 12/210,965

(22) Filed: Sep. 15, 2008

(65) Prior Publication Data

US 2009/0124594 A1    May 14, 2009

Related U.S. Application Data

(60) Provisional application No. 60/997,072, filed on Oct. 1, 2007, provisional application No. 60/997,071, filed on Oct. 1, 2007.

(51) Int. Cl.
*A61K 31/397* (2006.01)
(52) U.S. Cl. .................................. 514/210.15
(58) Field of Classification Search .............. 514/210.15
See application file for complete search history.

(56) References Cited

U.S. PATENT DOCUMENTS

| | | |
|---|---|---|
| 5,152,456 A | 10/1992 | Ross et al. |
| 5,261,601 A | 11/1993 | Ross et al. |
| 5,518,179 A | 5/1996 | Humberstone et al. |
| 6,660,249 B2 | 12/2003 | Montgomery |
| 6,962,151 B1 | 11/2005 | Knoch et al. |
| 6,983,747 B2 | 1/2006 | Gallem et al. |
| 7,138,419 B2 | 11/2006 | Montgomery et al. |
| 7,208,141 B2 | 4/2007 | Montgomery |
| 7,214,364 B2 | 5/2007 | Montgomery |
| 7,427,633 B2 | 9/2008 | Montgomery |
| 2007/0185076 A1 | 8/2007 | Montgomery |
| 2008/0050439 A1 | 2/2008 | Montgomery |

FOREIGN PATENT DOCUMENTS

| | | |
|---|---|---|
| WO | WO-01/34232 | 5/2001 |
| WO | WO-2005/007132 | 1/2005 |

OTHER PUBLICATIONS

Am. J. Respir. Crit. Care Med. (1995) "Standardization of Spirometry" 152: 1107-1136.
Burns, J. et al. (1998) "Microbiology of Sputm from Patients at Cystic Fibrosis Centers in the US" Clin Infect Dis. 27:158-163.
Chang, J. et al. (1999) "Assessment of Health-Related Quality of Life in Patients with Interstitial Lung Disease" Chest 116(5) 1175-1182.
Clement, A. et al. (2006) "Long Term Effects of Azithromycin in Patients with Cystic Fibrosis: a Double Blind, Placebo Controlled Trial" Thorax 61:895-902.
Donaldson, S. et al. (2006) "Mucus Clearance and Lung Function in Cystic Fibrosis with Hypertonic Saline" NEJM 354(3): 241-250.
Elkins, M. et al. (2006) "A Controlled Trial of Long-Term Inhaled Hypertonic Saline in Patients with Cystic Fibrosis" NEJM 354(3): 229-240.
Fuchs, H. et al. (1994) "Effect of Aerosolized Recombinant Human DNase on Exacerbations of Respiratory Symptoms and on Pulmonary Function in Patients with Cystic Fibrosis" NEJM 331(10): 637-642.
Gibson, R. et al. (2003) "Pathophysiology and Management of Pulmonary Infections in Cystic Fibrosis" Am J Respir Crit Care Med 168: 918-951.
Gibson, R. et al. (2006) "Microbiology, Safety and Pharmacokinetics of Aztreonam Lysinate for Inhalation in Patients with Cystic Fibrosis" Ped Pulm 41:656-665.
Gilead Press Release (2006) "Gilead Announces Preliminary Results from Phase III Study of Aztreonam Lysine for Inhalation in Patients with Cystic Fibrosis".
Gilead Press Release (2007) "Gilead Announces Presentation of Positive Phase III Data on Aztreonam Lysine for Inhalation in Patients with Cystic Fibrosis".
Goss, C. and Quittner, A. (2007) "Patient-reported Outcomes in Cystic Fibrosis" Proc Am Thorac Soc. 4:378-386.
Guyatt, G. (2000) "Making Sense of Quality-of-Life Data" Med. Care 38(9) Suppl II:175-179.
Henry, B. et al. (2003) "Development of the Cystic Fibrosis Questionnaire (CGQ) for Assessing Quality of Life in Pediatric and Adult Patients" Qual Life Res 12: 63-76.
Hodson, M. et al. (2002) "A Randomised Clinical Trial of Nebulised Tobramycin or Colistin in Cystic Ribrosis" Eur Respir. J. 20:658-664.
Jaeschke, R. et al. (1989) "Ascertaining the Minimal Clinically Important Difference" Controlled Clin Trials 10:407-415.
Juniper, E. et al. (1993) "Measuring Quality of Life in Asthma" Am Rev Respir Dis 147:832-838.
Knudson, R. et al. (1983) "Changes in the Normal Maximal Expiratory Flow-Volume curve with Growth and Aging" 127: 725-734.
Lamb and Goa (1999) "Management of Patients with Cystic Fibrosis" Dis Manage Health Outcomes 6(2): 93-108.
McCoy, K. et al. (2007) "Aztreonam Lysine for Inhalation (AZLI) for CF Patients with *P. aeruginosa* (PA) Infection" Eur CFC Poster No. 40.
McCoy, K. et al. (2008) "Inhaled Aztreonam Lysine for Chronic Airway *Pseudomonas aeruginosa* in Cystic Fibrosis" Am J Repir Crit Care Med 178:921-928.
Modi, A. and Quittner,A. (2003) "Validation of a Disease-specific Measure of Health-Related Quality of Life for Children with Cystic Fibrosis" J Ped Psych 28(7): 535-546.
Modi,A. et al. (2005) "Multi-method Measurement of Treatment Adherence for Children with Cystic Fibrosis and Its Relationship to Health-related Quality of Life" Pediatric Pulmon S28:371.
Moss,R. (2001) "Administration of Aerosolized Antibiotics in Cystic Fibrosis Patients" Chest 120(3) Suppl. 107S.

(Continued)

*Primary Examiner* — Raymond J Henley, III
(74) *Attorney, Agent, or Firm* — Lorie Ann Morgan

(57) ABSTRACT

Provided is a method of treating the health-related quality-of-life (HRQOL) symptoms of a lung disease, comprising the administration of an inhalable aerosol of aztreonam lysine. The method is suitable for the short term and sustainable long term treatment of HRQOL symptoms.

14 Claims, 10 Drawing Sheets

OTHER PUBLICATIONS

Moss, R. (2002) "Long-Term Benefits of Inhaled Tobramycin in Adolescent Patients with Cystic Fibrosis" Chest 121(1): 55-63.

Prescribing Information (2001) TOBI.

Quittner and Buu (2002) "Effects of Tobramycin Solution for Inhalation on Global Ratings of Quality of Life in Patients with Cystic Fibrosis and *Pseudomonas aeruginosa* Infection" Ped. Pul. 33:269-276.

Quittner, A. et al. (2005) "Development and Validation of the Cystic Fibrosis Questionnaire in the US: A Health-related Quality-of-life Measure for Cystic Fibrosis" Chest 128(4): 2347-2354.

Ramsey, B. et al. (1993) "Efficacy of Aerosolized Tobramycin in Patients with Cystic Fibrosis" NEJM 328(24): 1740-1746.

Ramsey, B et al. (1999) "Intermittent Administration of Inhaled Tobramycin in Patients with Cystic Fibrosis" NEJM 340(1): 23-30.

Rosenfeld, M. et al. (2001) "Defining a Pulmonary Exacerbation in Cystic Fibrosis" J Ped 139(3): 359-365.

Smith, A. et al. (1989) "Safety of Aerosol Tobramycin Administration for 3 Months to Patients with Cystic Fibrosis" Ped. Pulm. 7:265-271.

International Search Report and Written Opinion for PCT/US2008/076431, Intl Filing Date Sep. 15, 2008/ mailed Dec. 9, 2008.

Business Wire (2010) "Gilead's Head-to-Head Study of Cayston Versus Tobramycin Inhalation Solution in Cystic Fibrosis Patients Achieves Co-Primary Efficacy Endpoint of Non-Inferiority," Jun. 18, 2010.

EP 08836327.0 Communication dated May 3, 2010.

US 7,973,029 B2

INHALED AZTREONAM LYSINE FOR THE TREATMENT OF DEFICITS IN HEALTH-RELATED QUALITY-OF-LIFE IN LUNG DISEASES

This application is filed under 35 U.S.C. 111(a) claiming the benefit under 35 U.S.C. 119(e) to provisional applications 60/997,072 filed Oct. 1, 2007 and 60/997,071 filed Oct. 1, 2007, each of which is incorporated by reference in their entirety.

FIELD OF INVENTION

The instant invention relates to the treatment, prevention, and improvement of the health-related quality-of-life (HRQOL) symptoms of lung diseases comprising the administration of aztreonam lysine for inhalation (AZLI).

BACKGROUND

Cystic fibrosis (CF) is the most common life-shortening genetic disorder in Caucasians with approximately 70,000 people affected worldwide. CF is a multisystem disease affecting the respiratory tract, the digestive system and the genito-urinary system. The major focus of treatment is the respiratory tract since, by age 24, nearly 80% of patients with CF have chronic *Pseudomonas aeruginosa* (PA) airway infection, which is associated with an accelerated decline in pulmonary function and is a significant predictor of mortality (2005 Annual Data Report to the Center Directors, Bethesda, Md., Cystic Fibrosis Foundation, Bethesda, Md. 2006; Pamukcu, A, Pediatr. Pulmonol. 1995; 19:10-5; Henry, R L, Pediatr. Pulmonol. 1992; 12:158-61).

Clinical management of CF has improved during the past 15 years. Increased standardization of care and a focus on maintenance therapies, including nutrition, combined with the introduction of dornase alfa in 1993, tobramycin inhalation solution (TIS)(TOBI®) in 1998, and widespread use of chronic azithromycin during the past five years have been associated with approximately an 8-year increase in median predicted survival age (to 36.5 years; 1990-2005) and an increase in median forced expiratory volume in 1 second ($FEV_1$) percent predicted of approximately 10% across all age groups (1990-2005)(Clement, A, Thorax 2006; 61:895-902; Gibson, R L, Am. J. Respir. Crit. Care Med. 2003; 168:918-51).

Conventional measures of clinical improvement in CF, such as $FEV_1$ and bacterial sputum density, that are directed exclusively to respiratory effects of the treatments, do not capture the broader impact of CF on a patient's physical, social, and emotional functioning and may also miss the effects of treatment on other systems that may be affected by the disease. These additional aspects of many lung diseases are measured with health-related quality-of-life (HRQOL) instruments that have been developed for CF, asthma, and other lung diseases (Chang, J A, Chest 1999, 116, 1175-1182; Juniper, E, Am. Rev. Respir. Dis., 1993, 147, 832-838; Henry, B, Qual. Life Res., 2003, 12, 63-76). These measurements reflect an individual's subjective evaluation of his or her daily functioning and well-being, i.e., patient centered evaluation rather than physician centered evaluation. In chronic diseases, some treatments may produce benefits in activities of daily living that are not reflected in conventional medical measurements. For instance, clinical interventions to increase calorie intake to produce changes in weight and height in young children may increase energy levels and the ability to participate in sports in some individuals. Such an outcome is often more exciting for the families than simple weight or height gains. A patient's perception of improvements in daily functioning may also increase adherence to complex and time-consuming treatment regimens for some individuals. In addition, HRQOL instruments provide a basis for evaluating the effectiveness of treatments that are time-consuming and use significant health care resources. This latter effect is important for comparing the cost-effectiveness of different treatments that can influence access to the treatments and reimbursement policies for the treatments. Therefore, there is a need to develop drugs that improve the scores of the HRQOL in patients with lung diseases irrespective of the conventional clinical measurements that may be differentially affected by treatment with the same or a different drug.

Effects on quality-of-life symptoms of CF can be measured with HRQOL instruments such as the CF Questionnaire-Revised (CFQ-R) (Quittner, Chest 2005, 128, 2347-2354). Disease-related quality-of-life symptoms of CF include eating and digestive disturbances, emotional and physical dysfunction, diminished health perceptions, respiratory disturbances, role/school dysfunction, diminished vitality, diminished social functioning, diminished weight, and other measures of quality of life such as increased treatment burden. These disease-related symptoms are of particularly relevance for patients with CF, who must adhere to complex, time-consuming medical regimens that affect their normal activities. Their perception of treatment benefit is likely to improve adherence to treatment regimens and influence their long-term health outcomes as measured by conventional clinical measurements as well as improve the cost effectiveness of their treatment choices (Modi, A C, Pediatr. Pulmonol. 2005; S28:371). Therefore, there is a need for therapies that generally improve the scores of the HRQOL of CF patients.

Aztreonam lysine for inhalation (AZLI) is a dry powder or aerosolized formulation of the monobactam antibiotic, aztreonam, and lysine (Montgomery, U.S. Pat. Nos. 6,660,249, 7,138,419, 7208,141, 7,214,364, U.S. patent application Ser. Nos. 11/732,234 and 11/729,698; each of which is incorporated by reference in their entirety). In the clinic, AZLI improved the clinical symptoms of CF including $FEV_1$ sputum *Pseudomonas aeruginosa* concentrations and the time to need for inhaled or intravenous antibiotics (Gilead press releases, Dec. 19, 2006 and Apr. 19, 2007; McCoy, K.; et al., 30$^{th}$ European Cystic Fibrosis Conference Jun. 13-16, 2007, Poster 40, Antalya, Turkey).

SUMMARY OF INVENTION

It has now been unexpectedly discovered that administration of AZLI to CF patients will improve their HRQOL scores. In a clinical trial described herein, cystic fibrosis patients that had been previously treated with prescribed courses of tobramycin inhalation solution (TIS) for pulmonary *Pseudomonas aeruginosa* infections were administered a 28 day course of TIS. The study evaluated how these patients responded to symptom domaines of the CFQ-R. At the end of the 28 day study, the mean CFQ-R-respiratory domain scores of the patients had decreased −1.47 points, indicating a worsening of this CFQ-R symptom domain, while the other conventional measures of clinical efficacy, $FEV_1$ and *Pseudomonas aeruginosa* (PA) sputum concentrations, had improved. Subsequently, these patients were enrolled in a double-blind, placebo-controlled study to evaluate the effects of AZLI on all of these same clinical effects over a 28 day course. In contrast to the TIS study, robust increases in the CFQ-R-respiratory domain scores were produced in the AZLI treated patients. The improvements in $FEV_1$ and *Pseudomonas aeruginosa* (PA) sputum concentrations in the AZLI treated patients were comparable to those reported in the registration trials for inhaled tobramycin (Ramsey, B W, New Engl. J. Med. 1999, 340, 23-30). Therefore, AZLI and TIS can produce comparable effects on conventional clinical measurements such as $FEV_1$ and PA sputum density but AZLI caused improvements in the scores of the CFQ-R not produced by antibacterial drugs such as TIS.

This clinical trial also demonstrated that there was only a modest to poor correlation between increases in CFQ-R respiratory scores and $FEV_1$ among patients being treated with AZLI indicating that AZLI is unexpectedly treating the patient's perception of the disease. This is a new and unexpected use for AZLI in the treatment of CF and lung disease and the poor correlation between a conventional clinical endpoint ($FEV_1$) and the increased CFQ-R scores shows that AZLI treats another component of lung disease that is separate from that measured by conventional clinical endpoints.

In a second randomized, double-blind, placebo-controlled clinical trial described herein, AZLI was administered for 28 days to cystic fibrosis patients that had not been intensively treated with other inhaled antibiotics. Both the conventional clinical parameters used in the trial discussed above and the CFQ-R symptom domains were evaluated in this study. Increases in the scores of eleven of the twelve CFQ-R symptom domains were seen in the AZLI treated patients compared to baseline and the scores in all twelve domains were higher than those in the placebo group. This demonstrates that AZLI produces increases in CFQ-R scores in cystic fibrosis patients that have not been intensively treated with other inhaled antibiotics.

This second clinical trial also demonstrated that AZLI is treating another feature of lung disease that is separate from that measured by conventional clinical endpoints. As in the first clinical trial, there was only a modest to poor correlation between increased CFQ-R respiratory scores and $FEV_1$ among patients being treated with AZLI indicating that AZLI is treating the patient's perception of the disease. In addition, the effect on the CFQ-R respiratory domain in this second clinical trial persisted for at least two weeks after discontinuation of the AZLI administration whereas the conventional clinical measure of effectiveness, PA sputum density, had returned to pretreatment concentrations. This again demonstrates a new and unexpected use for AZLI in the treatment of cystic fibrosis and lung disease and the poor correlation between a conventional clinical endpoint ($FEV_1$) and the CFQ-R effect and the persistence of the CFQ-R effect when PA density has returned to pretreatment levels shows that AZLI treats another feature of lung disease that is separate from that measured by conventional clinical endpoints.

In a third, open-label, clinical trial described herein, patients from the two trials discussed above were treated with multiple 28-day courses of AZLI alternating with 28 day drug holidays. Conventional clinical parameters used in the trials discussed above and the CFQ-R respiratory domain were evaluated in this study. AZLI consistently produced increases in the CFQ-R respiratory domain scores during each of the treatment periods demonstrating that AZLI produces sustainable effects on HRQOL in cystic fibrosis patients over multiple courses of treatment. Also unexpected, during the 28 day drug holidays, the CFQ-R respiratory domain scores did not decrease to the base line levels seen when the patients entered the study showing that the effects of AZLI persist long after the discontinuation of drug treatment. The sustained increases in CFQ-R scores over multiple cycles of treatment is in contrast to the effects on the conventional measures of clinical efficacy, lung function ($FEV_1$) and PA sputum density, where there is an attenuated response after multiple cycles. The attenuated $FEV_1$ and PA sputum density responses over multiple cycles were expected with an antibiotic treatment since in the TSI registration trials, lung function and bacterial density changes were attenuated by the third on cycle of treatment. This further distinguishes the CFQ-R effects of AZLI from its antibiotic effects and shows that AZLI unexpectedly treats another feature of cystic fibrosis and lung disease that is separate from that measured by lung function and bacterial density in sputum.

The difference seen between the twice daily and three times daily treatment with AZLI is also unexpected. The increase in CFQ-R respiratory domain scores by the third treatment cycle is maintained in the three times daily group, but is greatly attenuated in the twice daily group. This is unexpected and is the first time a regimen response has been seen in a CF inhaled antibiotic trial.

Therefore, AZLI produces unexpected HRQOL clinical effects not produced by other inhaled antibacterial drugs in cystic fibrosis patients. These HRQOL effects persist even after discontinuation of the AZLI treatment when conventional measures of clinical efficacy have returned to pretreatment levels and the HRQOL effects are sustained over multiple courses of treatment when responses to conventional clinical measures are attenuated demonstrating that AZLI treats features of cystic fibrosis and lung disease that is separate from its antibacterial effects.

The object of the instant invention is to provide a method for preventing, ameliorating, or therapeutically treating at least one or more of the health-related quality-of-life symptoms of a lung disease, in a patient in need thereof comprising administering aztreonam lysine by inhalation. Non-limiting examples of lung disease include asthma, chronic obstructive pulmonary disease (COPD), cystic fibrosis, bronchiectasis, ventilator associated pneumonia, asthma, emphysema, chronic bronchitis, and idiopathic pulmonary fibrosis.

DETAILED DESCRIPTION OF THE INVENTION

CFQ-R Description

Figure 1:
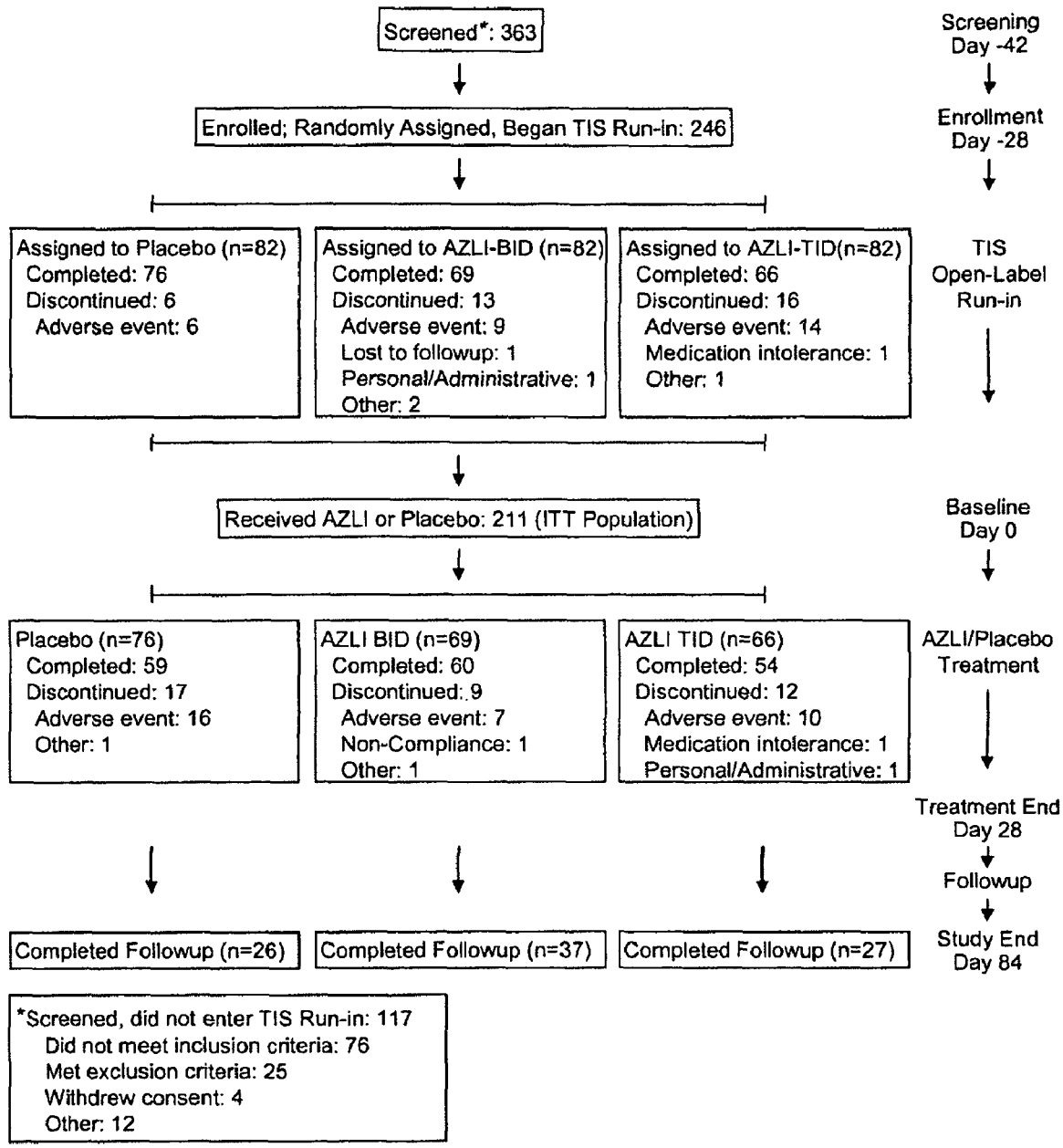
FIG. 1. Study Design and Patient Disposition for Clinical Trial I. Patients were randomly assigned to treatment with AZLI/placebo before they all began the open-label TIS run-in; their reasons for discontinuing during the TIS run-in are displayed by randomization group. The 211 patients remaining in the study at baseline (Day 0) received at least one dose of AZLI/placebo and comprise the intent to treat (ITT) population.

The CFQ-R is a validated health-related quality-of-life measure that meets recent FDA draft guidelines on patient-reported outcomes (Henry, B., *Qual. Life Res.* 2003, 12:63-76; Quittner, A. L., *Chest,* 2005, 128:2347-54; Modi A. C., *J. Ped. Psychol.* 2003, 28:535-46; Quittner, A. L., Cystic Fibrosis Foundation. CFQ-R cystic fibrosis questionnaire: a health-related quality of life measure, 2000). The domains include physical, vitality, emotion, eating, treatment burden, health perception, social, body image, role/school, weight, respiratory, and digestion. The number of domains varies depending on the CFQ-R format being used. The four formats of the questionnaire used to collect the data on the eCRF are:

Self-Administered:
Children ages 6 to 13 (to be completed by the parent or caregiver, self-report format)
Children ages 12 and 13 (to be completed by the child)
Adolescents and adults ages 14 and above (to be completed by the patient)

Interviewer-Administered:
Children 6 to 11 (to be completed by the research nurse or study coordinator, interviewer format)

For children, the interviewer-administered format (ages 6 to 11) and the questionnaire completed by the child (for ages 12 and 13) are identical. For the purpose of reporting, the results from these two formats will be combined and referred to as "Child" version. Questions associated with each domain in each CFQ-R version are shown in Table 1.

TABLE 1

CFQ-R Questions in Each Domain

| Domain | Version | | |
|---|---|---|---|
| | Parent/caregiver | Child | Teen/Adult |
| Physical | 1-5, 13-16 | 1-6 | 1-5, 13, 19-20 |
| Vitality | 8-31 | — | 6, 9-11 |
| Emotion | 6-7, 23, 25-26 | 7-14 | 7-8, 12, 31, 33 |

TABLE 1-continued

CFQ-R Questions in Each Domain

| Domain | Version | | |
|---|---|---|---|
| | Parent/caregiver | Child | Teen/Adult |
| Eating | 17, 44 | 15, 17, 19 | 14, 21, 50 |
| Treatment Burden | 18, 30-31 | 16, 18, 30 | 15-17 |
| Health Perceptions | 22, 24, 32 | — | 18, 32, 34 |
| Social | — | 20-26 | 22-23, 27-30 |
| Body Image | 19-21 | 27-29 | 24-26 |
| Role/School | 27-29 | — | 35-38 |
| Weight | 33 | — | 39 |
| Respiratory | 34-36, 38-40 | 31-34 | 40-42, 44-46 |
| Digestion | 41-43 | 35 | 47-49 |

Scaled scores for each CFQ-R domain will be calculated as follows:

The response (score) of each question will be allocated as 1 to 4 in the order in which they appear on the CFQ-R. For questions with an assigned number designated for each specific response, that number will be the response score. Parent/caregiver version, Question 37 (SAS Program Codes for Scoring the CFQ-R Parent/caregiver Version, CFQ-R handbook [Section 13.3.2]) and Teen/Adult version, Question 43 (SAS Program Codes for Scoring the CFQ-R Teen/Adult Version, CFQ-R handbook [Section 13.3.2]) will not be part of the relevant domain score. The responses of the questions in Table 2 will be reverse scored:

TABLE 2

CFQ-R Reversed Scores

| Version | Questions with Scores Reversed |
|---|---|
| Parent/Caregiver | 6, 10, 12, 15, 22, 24, 28, 31, 32 |
| Child | 1, 2, 3, 4, 5, 14, 18, 19, 20, 22, 24, 26 |
| Teen/Adult | 6, 10, 13, 15, 17, 18, 23, 28, 30, 32, 34, 35 | i.e., for the above question responses, a score of 1 will be set to 4, a score of 2 will be set to 3, a score of 3 will be set to 2, and a score of 4 will be set to 1.

If participants skip a question, the response will be set to missing. Missing values will be imputed with the median value of all completed responses in the relevant domain. If the median is not an integer in the case of a tie, the value will be set to the lower integer, for example a median of 2.5 should be set to 2. If more than half of the responses in a particular domain are missing, no values will be imputed and no domain score will be calculated.

The scaled domain score will be calculated (if at least half the domain responses are non-missing) as:

$$100 \left( \frac{\text{Sum of responses in domain} - \text{number of questions in domain} (n)}{\text{Maximum possible sum for domain} (4n) - n} \right).$$

ASPECTS OF THE INVENTION

In one aspect, the invention provides a method of treating at least one of the health-related quality-of-life symptoms of a lung disease, in a patient in need thereof, comprising administering a therapeutically effective amount of an inhalable dry powder or aerosol comprising about 1 to about 250 mg of aztreonam lysine per one dose to the airways of the lung endobronchial space.

In another aspect, the invention provides a method of treating at least one of the health-related quality-of-life symptoms of a lung disease, in a patient in need thereof comprising administering a therapeutically effective amount of an inhalable dry powder or aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In another embodiment of this aspect, the patient has a chronic pulmonary bacterial infection caused by gram-negative bacteria. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising mass median aerodynamic diameters (MMAD) of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in 1 mL of saline comprising about 0.17%, w/v, sodium chloride and delivered by an electronic nebulizer adapted to deliver predominantly aerosol particles sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 14 consecutive days wherein each inhalable aerosol dose comprises about 75 mg of aztreonam dissolved in 1 mL of saline comprising about 0.17%, w/v, sodium chloride and is delivered by an electronic nebulizer adapted to deliver predominantly aerosol particle sizes comprising MMAD of about 1 to about 5 μm.

In another aspect, the invention provides a method of treating at least one of the health-related quality-of-life symptoms of cystic fibrosis, in a cystic fibrosis patient in need thereof, comprising administering a therapeutically effective amount of an inhalable dry powder or aerosol comprising about 1 to about 250 mg of aztreonam lysine per one dose to the airways of the lung endobronchial space.

In another aspect, the invention provides a method of treating at least one of the health-related quality-of-life symptoms of cystic fibrosis, in a patient in need thereof, comprising administering a therapeutically effective amount of an inhalable dry powder or aerosol comprising about 1 to about 250 mg of aztreonam lysine per one dose to the airways of the lung endobronchial space wherein a dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day provided that a total dose of aztreonam lysine is not higher than about 750 mg a day. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 ing of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 14 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating one, two, three, four, five, six, seven, eight, nine, ten, eleven or all of the symptom domains of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect the invention provides a method of treating one, two, three, four, five, six, seven, eight, nine, ten, eleven or all of the symptom domains of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day provided that a total dose of aztreonam lysine is not higher than about 750 mg a day. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 14 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the respiratory symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the respiratory symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein a dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another embodiment of this aspect, the respiratory symptom domain score is increased by at least 5 points compared to the score at the beginning of the administration.

In another aspect, the invention provides a method of treating the body image symptom domain of the CF Questionaire-Revised, in a cystic fibrosis patient in need thereof comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the body image symptom domain of the CF Questionaire-Revised, in a cystic fibrosis patient in need thereof comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the digestion symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the digestion symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the eating symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the eating symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the emotional symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the emotional symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the health perceptions symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the health perceptions symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 pin. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the physical symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect the invention provides a method of treating the physical symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the role/school symptom domain of the CF Questionaire-Revised, in a cystic fibrosis patient in need thereof comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the role/school symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 μL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 μm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 μm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, W/V, sodium chloride and delivered by an electronic nebulizer adapted to deliver predominantly aerosol particle sizes comprising MMAD of about 1 to about 5 μm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 μm.

In another aspect, the invention provides a method of treating the social symptom domain of the CF Questionaire-Revised, in a cystic fibrosis patient in need thereof, comprising administering a therapeutically effective amount of a dairy powder or inhalable aerosol comprising about 1 to about 250 mg of aztreonam lysine per one dose to the airways of the lung endobronchial space.

In another aspect, the invention provides a method of treating the social symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 µm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 µm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In a particularly preferred embodiment of this aspect, a dose of inhalable aerosol is administered three times a day wherein each inhalable aerosol dose comprises about 75 mg of aztreonam dissolved in about 1 mL of saline composing about 0.17%, w/v, sodium chloride and delivered by an electronic nebulizer adapted to deliver predominantly aerosol particle sizes comprising MMAD of about 1 to about 5 µm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm.

In another aspect, the invention provides a method of treating the treatment burden symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the treatment burden symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect the inhalable aerosol is delivered by an electronic nebulizer adapted to deliver predominantly aerosol particle sizes comprising MMAD of about 1 to about 5 µm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 µm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm.

In another aspect, the invention provides a method of treating the vitality symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the vitality symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 µm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 µm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm.

In another aspect, the invention provides a method of treating the weight symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space.

In another aspect, the invention provides a method of treating the weight symptom domain of the CF Questionaire-Revised, in a cystic fibrosis patient in need thereof, comprising administering a therapeutically effective amount of a dry powder or inhalable aerosol comprising about 1 to about 250 mg of aztreonam lysine per one dose to the airways of the lung endobronchial space wherein the dose of inhalable dry powder or aerosol is administered 3 to 10 times a day for at least 14 to 28 consecutive days provided that the total daily dose does not exceed 750 mg per day. In one embodiment of this aspect, the inhalable aerosol comprises about 1 to about 250 mg of aztreonam lysine dissolved in about 1 to about 5 mL of a saline solution comprising about 0.1 to about 0.45%, w/v, of sodium chloride. In another embodiment of this aspect, the inhalable aerosol is delivered by a nebulizer. In another embodiment of this aspect, the inhalable aerosol is delivered by an electronic nebulizer adapted to deliver predominantly aerosol particle sizes comprising MMAD of about 1 to about 5 µm. In another embodiment of this aspect, a dose of inhalable aerosol is administered three to ten times a day wherein each dose comprises about 1 to about 250 mg of aztreonam lysine dissolved in about 1 to about 5 mL of a saline solution comprising about 0.1 to about 0.45%, w/v, of sodium chloride and delivered by an electronic nebulizer adapted to deliver predominantly aerosol particle sizes comprising MMAD of about 1 to about 5 µm. In a preferred embodiment of this aspect, a dose of inhalable aerosol is administered three to ten times a day wherein each inhalable aerosol dose comprises about 75 mg of aztreonam. In another preferred embodiment of this aspect, a dose of inhalable aerosol is administered three to ten times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In a particularly preferred embodiment of this aspect, a dose of inhalable aerosol is administered three times a day wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm. In another particularly preferred embodiment of this aspect, a dose of inhalable aerosol is administered three times a day for at least 28 consecutive days wherein each inhalable aerosol dose comprises about 75 mg of aztreonam dissolved in about 1 mL of saline comprising about 0.17%, w/v, sodium chloride and delivered by an electronic nebulizer adapted to deliver predominantly aerosol particle sizes comprising MMAD of about 1 to about 5 µm.

In another aspect, the invention provides a method of treating one, two, three, four, five, six, seven, eight, nine, ten, eleven or all of the symptom domains of the CF Questionaire-Revised, in a cystic fibrosis patient in need thereof, comprising administering a therapeutically effective amount of an inhalable aerosol of aztreonam lysine three to ten times a day for at least 14 to 28 consecutive days wherein each inhalable aerosol dose comprises about 75 mg of aztreonam dissolved in about 1 mL of saline comprising about 0.17%, w/v, sodium chloride and is delivered by an electronic nebulizer adapted to deliver predominantly aerosol particle sizes comprising MMAD of about 1 to about 5 µm. In one embodiment of this aspect, a dose of inhalable aerosol of aztreonam lysine is administered three to ten times a day for at least 28 consecutive days. In another embodiment of this aspect, the symptom domain of the CFQ-R is the respiratory domain. In another embodiment of this aspect, the symptom domain of the CFQ-R is the respiratory domain wherein the domain score is increased by at least 5 points compared to the beginning of the administration. In another embodiment of this aspect, the symptom domain of the CFQ-R is the physical domain. In another embodiment of this aspect, the symptom domain of the CFQ-R is the vitality domain. In another embodiment of this aspect, the symptom domain of the CFQ-R is the emotional domain. In another embodiment of this aspect, the symptom domain of the CFQ-R is the eating domain. In another embodiment of this aspect, the symptom domain of the CFQ-R is the treatment burden domain. In another embodiment of this aspect, the symptom domain of the CFQ-R is the health perceptions domain. In another embodiment of this aspect, the symptom domain of the CFQ-R is the social domain. In another embodiment of this aspect, the symptom domain of the CFQ-R is the body image domain. In another embodiment of this aspect, the symptom domain of the CFQ-R is the role/school domain. In another embodiment of this aspect the symptom domain of the CFQ-R is the weight domain. In another embodiment of this aspect, the symptom domain of the CFQ-R is the digestion domain.

In another aspect, the invention provides a method of treating one, two, three, four, five, six, seven, eight, nine, ten, eleven or all of the symptom domains of the CF Questionaire-Revised, in a cystic fibrosis patient in need thereof, comprising administering a therapeutically effective amount of an inhalable aerosol of aztreonam lysine three to ten times a day for at least 14 to 28 consecutive days wherein each inhalable aerosol dose comprises about 75 mg of aztreonam dissolved in about 1 mL of saline comprising about 0.17%, w/v, sodium chloride and is delivered by electronic nebulizer adapted to deliver predominantly aerosol particle sizes comprising MMAD of about 1 to about 5 µm and wherein the patient has a pulmonary *Pseudomonas aeruginosa* infection. In one embodiment of this aspect, a dose of inhalable aerosol of aztreonam lysine is administered three times a day for at least 28 consecutive days. In another embodiment of this aspect, the symptom domain of the CFQ-R is the respiratory domain. In another embodiment of this aspect, the symptom domain of the CFQ-R is the respiratory domain wherein the domain score is increased by at least 5 points relative to the beginning of the administration. In another embodiment of this aspect, the symptom domain of the CFQ-R is the physical domain. In another embodiment of this aspect, the symptom domain of the CFQ-R is the vitality domain. In another embodiment of this aspect, the symptom domain of the CFQ-R is the emotional domain. In another embodiment of this aspect, the symptom domain of the CFQ-R is the eating domain. In another embodiment of this aspect, the symptom domain of the CFQ-R is the treatment burden domain. In another embodiment of this aspect, the symptom domain of the CFQ-R is the health perceptions domain. In another embodiment of this aspect, the symptom domain of the CFQ-R is the social domain. In another embodiment of this aspect, the symptom domain of the CFQ-R is the body image domain. In another embodiment of this aspect, the symptom domain of the CFQ-R is the role/school domain. In another embodiment of this aspect, the symptom domain of the CFQ-R is the weight domain. In another embodiment of this aspect, the symptom domain of the CFQ-R is the digestion domain.

Drug Holiday Regimen

In one aspect of the invention, the treatments with AZLI are interspersed with courses of treatment with other drugs, particularly antibiotics, or with drug holidays, i.e., wherein no drugs are administered. By way of example and not limitation, the patient would be administered a standard prescribed course of tobramycin inhalation solution for 28 days followed by a 14 to 28 day course of treatment with AZLI. Alternatively, the patient would be administered a 14 to 28 day course of treatment with AZLI followed by a standard prescribed course of tobramycin inhalation solution (28 days) Alternatively, the patient would be administered a 14 to 28 day course of treatment with AZLI followed by a 14 to 28 day drug holiday wherein no drug would be administered. All of these alternating courses of treatment could be recursive. That is, they could be applied one, two, three, four, five, six, seven, eight, nine or more times.

In another aspect, the invention provides a method of treating one, two, three, four, five, six, seven, eight, nine, ten, eleven or all of the symptom domains of the CF Questionaire-Revised, in a cystic fibrosis patient in need thereof, wherein the patient has a pulmonary *Pseudomonas aeruginosa* infection, comprising administering a therapeutically effective amount of an inhalable aerosol aztreonam lysine three to ten times a day for at least 14 to 28 consecutive days wherein each inhalable aerosol dose comprises about 75 mg of aztreonam dissolved in about 1 mL of saline comprising about 0.17%, w/v, sodium chloride and is delivered by electronic nebulizer adapted to deliver predominantly aerosol particle sizes comprising MMAD of about 1 to about 5 µm. In one embodiment of this aspect, a dose of inhalable aerosol of aztreonam lysine is administered three to ten times a day for at least 28 consecutive days. In another embodiment of this aspect, a dose of inhalable aerosol of aztreonam lysine is administered three times a day for at least 28 consecutive days. In another embodiment of this aspect, the symptom domain of the CFQ-R is the respiratory domain. In another embodiment of this aspect, the symptom domain of the CFQ-R is the respiratory domain and a dose of inhalable aerosol is administered three times a day. In another embodiment of this aspect, the symptom domain of the CFQ-R is the respiratory domain wherein the domain score is increased by at least 5 points relative to the beginning of the inhalable aerosol administration. In another embodiment of this aspect, the symptom domain of the CFQ-R is the respiratory domain wherein the domain score remains increased after a patient's *Pseudomonas aeruginosa* sputum density has increased to pretreatment concentrations after the cessation of the inhalable aerosol administration. In another embodiment of this aspect, the symptom domain of the CFQ-R is the physical domain. In another embodiment of this aspect, the symptom domain of the CFQ-R is the vitality domain. In another embodiment of this aspect, the symptom domain of the CFQ-R is the emotional domain. In another embodiment of this aspect, the symptom domain of the CFQ-R is the eating domain. In another embodiment of this aspect, the symptom domain of the CFQ-R is the treatment burden domain. In another embodiment of this aspect, the symptom domain of the CFQ-R is the health perceptions domain. In another embodiment of this aspect, the symptom domain of the CFQ-R is the social domain. In another embodiment of this aspect, the symptom domain of the CFQ-R is the body image domain. In another embodiment of this aspect, the symptom domain of the CFQ-R is the role/school domain. In another embodiment of this aspect, the symptom domain of the CFQ-R is the weight domain. In another embodiment of this aspect, the symptom domain of the CFQ-R is the digestion domain. In another embodiment of this aspect, the cystic fibrosis patient is previously treated with a prescribed course of tobramycin inhalation solution for 28 consecutive days. In another embodiment of this aspect, the cystic fibrosis patient is treated for 14 to 28 consecutive days with AZLI followed by a standard prescribed course of tobramycin inhalation solution for 28 consecutive days.

In another aspect, the invention provides a method of treating one, two, three, four, five, six, seven, eight, nine, ten, eleven or all of the symptom domains of the CF Questionaire-Revised, in a cystic fibrosis patient in need thereof, wherein the patient has a pulmonary *Pseudomonas aeruginosa* infection, comprising a dosing regimen of administering a therapeutically effective amount of an inhalable aerosol of aztreonam lysine three to ten times a day for at least 14 to 28 consecutive days followed by a 14 to 28 consecutive day drug holiday wherein each inhalable aerosol dose comprises about 75 mg of aztreonam dissolved in about 1 mL of saline comprising about 0.17%, w/v, sodium chloride and is delivered by an electronic nebulizer adapted to deliver predominantly aerosol particle sizes comprising MMAD of about 1 to about 5 µm. In another embodiment of this aspect, the symptom domain of the CFQ-R is the respiratory domain. In another embodiment of this aspect, the symptom domain of the CFQ-R is the respiratory domain and a dose of inhalable aerosol is administered three times a day. In another embodiment of this aspect, the symptom domain of the CFQ-R is the respiratory domain wherein the domain score is increased by at least 5 points relative to the beginning of the inhalable aerosol administration. In another embodiment of this aspect, the symptom domain of the CFQ-R is the respiratory domain wherein the domain score remains increased after a patient's *Pseudomonas aeruginosa* sputum density has increased to at least pretreatment concentrations after the cessation of the inhalable aerosol administration. In another embodiment of this aspect, the symptom domain of the CFQ-R is the physical domain. In another embodiment of this aspect, the symptom domain of the CFQ-R is the vitality domain. In another embodiment of this aspect, the symptom domain of the CFQ-R is the emotional domain. In another embodiment of this aspect, the symptom domain of the CFQ-R is the eating domain. In another embodiment of this aspect, the symptom domain of the CFQ-R is the treatment burden domain. In another embodiment of this aspect, the symptom domain of the CFQ-R is the health perceptions domain. In another embodiment of this aspect, the symptom domain of the CFQ-R is the social domain. In another embodiment of this aspect, the symptom domain of the CFQ-R is the body image domain. In another embodiment of this aspect, the symptom domain of the CFQ-R is the role/school domain. In another embodiment of this aspect, the symptom domain of the CFQ-R is the weight domain. In another embodiment of this aspect, the symptom domain of the CFQ-R is the digestion domain. In another embodiment of this aspect, the dosing regimen is repeated one, two, three, four, five, six, seven, eight or nine times.

In another aspect, the invention provides a method of treating the respiratory symptom domain of the CF Questionaire-Revised, in a cystic fibrosis patient in need thereof wherein the patient has a pulmonary *Pseudomonas aeruginosa* infection comprising administering a therapeutically effective amount of an inhalable aerosol of aztreonam lysine three to ten times a day for at least 14 to 28 consecutive days wherein each inhalable aerosol dose comprises about 75 mg of aztreonam dissolved in about 1 mL of saline comprising about 0.17%, w/v, sodium chloride and is delivered by an electronic nebulizer adapted to deliver predominantly aerosol particle sizes comprising MMAD of about 1 to about 5 μm. In another embodiment of this aspect, a dose of inhalable aerosol is administered three to ten times a day for at least 28 consecutive days. In another embodiment of this aspect, a dose of inhalable aerosol is administered three times a day. In another embodiment of this aspect, the respiratory domain score is increased by at least 5 points relative to the beginning of the inhalable aerosol administration. In another embodiment of this aspect, the respiratory domain score remains increased after a patient's *Pseudomonas aeruginosa* sputum density has increased to at least pretreatment concentrations after the cessation of the inhalable aerosol administration. In another embodiment of this aspect, the cystic fibrosis patient was previously treated with a prescribed course of tobramycin inhalation solution for 28 consecutive days. In another embodiment of this aspect, the cystic fibrosis patient was previously treated with a prescribed course of tobramycin inhalation solution for 28 consecutive days and the respiratory domain score is increased by at least 5 points from the stall of the administration of the inhalable aerosol of aztreonam lysine.

In another aspect, the invention provides a method of treating the respiratory symptom domain of the CF Questionaire-Revised, in a cystic fibrosis patient in need thereof wherein the patient has a pulmonary *Pseudomonas aeruginosa* infection, comprising a dosing regimen of administering a therapeutically effective amount of an inhalable aerosol of aztreonam lysine three to ten times a day for at least 14 to 28 consecutive days followed by a 14 to 28 consecutive day drug holiday wherein each inhalable aerosol dose comprises about 75 mg of aztreonam dissolved in about 1 mL of saline comprising about 0.17%, w/v, sodium chloride and is delivered by an electronic nebulizer adapted to deliver predominantly aerosol particle sizes comprising MMAD of about 1 to about 5 μm. In another embodiment of this aspect, a dose of inhalable aerosol is administered three times a day. In another embodiment of this aspect, the respiratory domain score is increased by at least 5 points after the administration of the inhalable aerosol. In another embodiment of this aspect, the respiratory domain score remains increased after a patient's *Pseudomonas aeruginosa* sputum density has increased to at least pretreatment concentrations after the cessation of the inhalable aerosol administration. In another embodiment of this aspect, the dosing regimen is repeated one, two, three, four, five, six, seven, eight or nine times. In another embodiment of this aspect, the dosing regimen is repeated one, two, three, four, five, six, seven, eight or nine times and the respiratory domain score during at least one dosing regimen is increased by at least 5 points compared to the score at the beginning of at least one of the dosing regimens. In another embodiment of this aspect, the dosing regimen is repeated one, two, three, four, five, six, seven, eight or nine times and the respiratory domain score during at least one dosing regimen remains increased after a patient's *Pseudomonas aeruginosa* sputum density has increased to at least pretreatment concentrations during the drug holiday. In another embodiment of this aspect, the respiratory domain score after an inhalable aerosol administration remains above the respiratory domain score before the inhalable aerosol administration for the entire drug holiday. In another embodiment of this aspect, the inhalable aerosol of aztreonam lysine is administered three times a day for at least 28 consecutive days.

Aztreonam Lysine for Inhalation (AZLI)

As used herein, unless otherwise indicated, aztreonam lysine and aztreonam lysinate are synonymous. Aztreonam lysine for inhalation is a white to off-white powder formed by combining alpha-aztreonam with L-lysine (Montgomery, U.S. Pat. Nos. 6,660,249, 7,138,419, 7,208,141, 7,214,364, U.S. patent application Ser. Nos. 11/732,234 and 11/729,698; each of which is incorporated by reference herein in their entirety). The resulting product is a 1.9:1 molar ratio of L-lysine monohydrate to aztreonam. Therefore, by way of example and not limitation, in a preferred single dosage form, the aztreonam lysine for inhalation comprises 75 mg of aztreonam and 52.5 mg of L-lysine monohydrate (46.7 mg of L-lysine).

AZLI is suitable for efficacious delivery to the airways of the lung endobronchial space by aerosolization or as a dry powder. Most preferably, AZLI is suitable for formulation as a concentrated aztreonam lysine for aerosolization by atomizing, jet, ultrasonic, pressurized, vibrating porous plate or equivalent nebulizers or by dry powder inhalers which predominantly produce aztreonam lysine aerosol or dry powder particles comprising MMAD of about 1 to about 5 μm.

The AZLI may be endobronchially administered in a dry powder that has been formulated for efficacious delivery of the finely milled AZLI powder into the endobronchial space using a dry powder or metered dose inhaler. For delivery of a dry powder, the AZLI in the formulation is milled, precipitated, spray dried or otherwise processed to particle sizes comprising predominantly MMAD of about 1 to about 5 μm.

AZLI compositions for aerosolization are formulated for efficacious delivery of aerosolized aztreonam lysine to the airways of the lung endobronchial space. The aerosol formulation is delivered in a total volume of between about 1 and about 5 mL of aqueous physiologically acceptable solution for one inhalation dose. When formulated and delivered according to the method of invention, it delivers a therapeutically efficacious dose of aztreonam lysine to the airways of the lung endobronchial space to treat the health-related quality-of-life symptoms of cystic fibrosis, in a patient in need thereof.

The aerosolizable formulations contain a minimal yet efficacious amount of aztreonam lysine from about 1 to about 250 mg, more preferably from about 25 to about 150 mg/mL, and most preferably about 122 mg/mL; formulated in the smallest possible volume of physiologically acceptable diluent having a certain degree of salinity and a certain pH range. The concentration of aztreonam lysine, salinity, and pH range is adjusted to permit generation of an aztreonam lysine aerosol that is well tolerated by patients and that minimizes the development of undesirable side effects such as bronchospasm and cough.

In a non-limiting, preferred single dose formulation, AZLI is dissolved in about 1 mL of about 0.17% sodium chloride, w/v, just prior to administration by aerosolization.

A combination of the aqueous formulations of AZLI with the atomizing, jet, pressurized, vibrating porous plate, ultrasonic, or electronic nebulizer permits, depending on the nebulizer, about at least 20 to about 90%, most typically 70%, delivery of the administered dose of aztreonam lysine into the airways of the lung.

Devices for Delivery of AZLI
Nebulizers

Compositions of the invention described above provide the AZLI formulated in a solution permitting delivery of a therapeutically effective amount of aztreonam lysine provided that the aerosol generated by nebulization meets criteria required for efficient delivery of the drug. Therefore, the nebulizer which aerosolizes the formulation of AZLI becomes an important feature of the invention. Although many nebulizer types are commercially available, not all are suitable for practicing the instant invention.

A nebulizer is selected primarily on the basis of its ability to aerosolize the aqueous AZLI formulation into particles comprising a MMAD predominantly between about 1 and about 5 μm. Jet, ultrasonic, and atomizing nebulizers have been developed that produce aerosol particles with the required predominant MMAD.

The nebulizer must also be efficient in generating the aerosol of required particle sizes from a concentrated small volume of formulation to limit drug cost and time required to administer an efficacious dose. A combination of an aqueous AZLI formulation and a nebulizing device significantly enhances the efficiency and speed of aztreonam lysine administration. For example, the average time for administration of other aerosolized drugs such as tobramycin is 15-20 minutes per dose. The time required for this treatment represents a significant burden to the patient and contributes to reduced compliance with the prescribed twice a day regimen. Furthermore, the nebulizer system used for tobramycin administration is less efficient than new atomizing devices. The total dose of tobramycin deposited in the lung is in the 12 to 15% range; approximately 30% of the dispensed drug remains in the nebulizer at the end of treatment; and, of the portion of drug aerosolized, about 30% is emitted as particles too large or small to reach the lower airways.

Typical nebulizing devices suitable for practicing the instant invention include atomizing nebulizers, modified jet nebulizers, ultrasonic nebulizers, and electronic nebulizers modified for handling small volumes of highly concentrated drug in a specific formulation having a specific pH, osmolality and salinity.

A particularly preferred nebulizer is the Pari eFlow® Electronic Nebulizer as disclosed in U.S. Pat. Nos. 5,152,456, 5,261,601, 5,518,179, 6,983,747, 6,962,151, and International Application WO01/034232; each of which is incorporated by reference herein in their entirety. This atomizing nebulizer, with an output of 8 to 10 μL/second, or 0.48 to 0.60 mL/minutes, is capable of delivering drug material 2 to 4 times faster than earlier nebulizers such as the PARI LC plus Nebulizer®. Furthermore, this nebulizer is able to aerosolize approximately 90% of the dispensed dose, with 85% or more of the aerosol particles being with the size range required for lower airway deposition. Administration of a specifically designed formulation of AZLI, such as those described herein, using the eFlow Nebulizer leads to a substantial improvement in lower airway delivery and to treatment times as short as three or four minutes.

Dry Powder Inhalers

There are two major designs for dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of the drug into small particles with MMAD from about 1 to about 5 μm, and usually involve co-formulation with larger excipient particles such as 100 μm diameter lactose particles. Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

Current technology for dry powder inhalers is such that payload limits are around 100 mg of powder. Therefore multiple activations of the dry powder inhalers and subsequent patient inspirations may be required to provide efficacious doses of aztreonam lysine with these devices.

DEFINITIONS

Unless stated otherwise, the following terms and phrases as used herein are intended to have the following meanings:

When trade names are used herein, applicants intend to independently include the tradename product and the active pharmaceutical ingredient(s) or device of the tradename product.

The term "aerosol", as used herein, unless otherwise indicated, means a suspension of fine liquid or solid particles or combinations thereof in a gas. As used herein, the term shall also incorporate the formulation that is used in generating the aerosol.

The term "inhalable aerosol", as used herein, unless otherwise indicated, means an aerosol as defined above that is adapted to be physiologically acceptable. Important non-limiting aspects in making an inhalable aerosol physiologically acceptable include pH, osmolality, and permeable anion concentration. As used herein, the term shall also incorporate the formulation that is used in generating the inhalable aerosol.

The term "treating", as used herein, unless otherwise indicated, means reversing, alleviating, inhibiting the progress of, or preventing the disorder or condition to which such term applies, or one or more symptoms of such disorder or condition. A non-limiting example of "treating" is to increase the score of one or more domains of an HRQOL instrument. The term "treatment", as used herein, refers to the act of treating, as "treating" is defined immediately above.

The term "therapeutically effective amount", as used herein, is the amount of aztreonam lysine present in a composition described herein, such as an inhalable aerosol, that is needed to provide a desired level of drug in the secretions and tissues of the airways and lungs, or alternatively, in the bloodstream of a subject to be treated to give an anticipated physiological response, desired biological effect, or improvement in a domain of a HRQOL instrument when such a composition is administered by inhalation. The precise amount will depend upon numerous factors, for example the particular formulation, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "MMAD" means mass median aerodynamic diameter.

The term "predominantly" or "predominant" when referring to particle size, means including at least 70% but preferably 90% of particle sizes between 1 µm and 5 µm.

The term "w/v" means weight to volume.

The modifier "about" used in connection with a quantity is inclusive of the stated value and has the meaning dictated by the context (e.g., includes the degree of error associated with measurement of the particular quantity).

The term "prescribed course(s)" means the course of treatment indicated on the label or package insert of a registered drug.

The term "CFQ-R" or "CF-Questionaire-Revised" means the HRQRL instrument Cystic Fibrosis Questionaire-Revised.

The term "TIS" means tobramycin inhalation solution, USP or TOBI®.

The term "drug holiday" means that a patient stops taking a medication for a period of time.

The term "*Pseudomonas aeruginosa* sputum density" or "PA sputum density" means the concentration of *Pseudomonas aeruginosa* in the sputum of a patient as determined by the number of colony forming units (CFU) in a standardized microbiological culture for *Pseudomonas aeruginosa*.

EXAMPLES

Introduction

Clinical Trial 1

The study described herein included patients with CF who frequently utilized antibiotics for PA airway infections, assessing the effectiveness of AZLI in this intensively-treated patient population. Early treatment of pulmonary exacerbations has resulted in fewer hospitalizations; thus time to hospitalization has become less clinically relevant as a study endpoint. Therefore, clinical deterioration was assessed with a new measure: time to need for additional antipseudomonal antibiotics to treat symptoms indicative of pulmonary exacerbation (Rosenfeld, M, J. Pediatr 2001; 139:359-65). Patient-reported improvements in clinical symptoms were measured with the Cystic Fibrosis Questionnaire-Revised (CFQ-R), a validated health-related quality-of-life measure. An established efficacy measure, change in $FEV_1$ was also included in the study. This combination of endpoints provided a broad view of patient responses to AZLI therapy. The clinical study described later under Clinical Trial II assessed the safety and efficacy of AZLI to treat PA airway infection in patients with CF who infrequently utilized antipseudomonal-maintenance therapy.

Methods
Study Design

This randomized, double-blind, placebo-controlled, study was conducted at 56 US CF centers (February, 2005-September, 2006). After screening (Day −42, FIG. 1), eligible patients were enrolled (Day −28), randomly assigned to 75 mg AZLI (twice [BID] or three times [TID] daily) or placebo (1:1:1), and began treatment with open-label TIS (Day −28). At baseline (Day 0), patients completed the course of TIS and began the randomized AZLI/placebo treatment. Patients were monitored mid-treatment (Day 14), at end of treatment (Day 28), and during followup (Days 42, 56, 70, 84).

A complete physical examination was performed at screening. Spirometry (American Thoracic Society standards) was performed at every study visit (before and 30 minutes after any treatment) (Am J Respir Crit. Care Med 1995; 152:1107-36). $FEV_1\%$ predicted values were calculated using the Knudson equation (Knudson, R J, Am Rev Respir Dis 1983; 127:725-34).

TIS (300 mg, BID) was administered with the PARI LC® PLUS Jet nebulizer and AZLI (75 mg aztreonam, 52.5 mg lysine monohydrate) or placebo (5 mg lactose), diluted in 1 mL of 0.17% NaCl (BID or TID), with the eFlow® Electronic Nebulizer (PARI Innovative Manufacturers, Midlothian, Va.). Patients self-administered a bronchodilator at home before study medication and a short-acting β2-agonist 15 minutes before the first spirometry measurements at study visits. Patients continued any prescribed bronchodilator use, excluding the 6 hours before study visits.

TIS was dispensed on Day −28 and AZLI/placebo on Day 0; used and unused vials were subsequently collected to assess treatment compliance.

This study was conducted in compliance with the Declaration of Helsinki. Institutional Review Boards approved the study for each site and all patients or their guardians provided written informed consent prior to any study procedures. The ClinicalTrials.gov accession number is NCT00004520.

Study Population

Eligible patients (≧6 years, documented diagnosis of CF) had current PA airway infections, ≧3 TIS courses within the previous year, the ability to perform reproducible pulmonary function tests, and, at screening, $FEV_1 \geq 25\%$ and ≦75% predicted values and arterial oxygen saturation ≧90% on room air. Chronic azithromycin use was allowed if the regimen was unchanged in the previous 3 months and if additional antipseudomonal therapy had been utilized since initiating azithromycin.

Exclusion criteria included current oral corticosteroid use (equivalent to >10 mg prednisone daily); airway cultures yielding *Burkholderia cepacia* complex in previous 2 years; oxygen supplementation: daily continuous or >2 L/minute at night; monobactam-antibiotic hypersensitivity; inhaled short-acting β2-agonist intolerance; recent changes in antimicrobial, bronchodilator, anti-inflammatory, corticosteroid medications or physiotherapy technique/schedule; lung transplantation; new finding on chest radiograph at screening; AST or ALT >5-times or serum creatinine >2-times upper limit of normal (at screening); pregnancy; lactation; or, in opinion of investigator, medical or psychiatric illness interfering with study participation.

Efficacy Measures

The primary efficacy endpoint was time to need for additional inhaled or IV antipseudomonal antibiotics to treat symptoms indicative of pulmonary exacerbation. The predefined list of symptoms included decreased exercise tolerance, increased cough, increased sputum production/chest congestion, or decreased appetite. Major secondary efficacy endpoints included changes in clinical symptoms (CFQ-R-Respiratory Symptoms Scale), pulmonary function, PA density (colony forming units (CFU)/gram sputum, $log_{10}$ transformed), time to hospitalization, hospitalizations, and weight. Scores for CFQ-R Scales ranged from 0 to 100; increasing scores indicated improvement. The CFQ-R was administered at the beginning of study visits to minimize any influence of physiological data or study personnel on patient responses. Using responses during the TIS phase to a Global Rating of Change Questionnaire (GRCQ)-Respiratory Domain, a minimal clinically important difference (MCID) score of 5 was determined for the CFQ-R-Respiratory Scale; thus 5 point changes indicated improving/worsening respiratory symptoms (Guyatt, G H, Med Care 2000:II:175-9; Jaeschke, R, Control Clin Trials 1989; 10:407-15).

Microbiological endpoints included the minimum inhibitory concentration (MIC) of aztreonam for PA, and the prevalence of other pathogens.

Safety Measures

Safety was assessed by monitoring adverse events and changes in clinical laboratory values, vital signs, and airway reactivity. Worsening CF symptoms were treated as adverse events and patients were withdrawn from the study if they exhibited any of the predefined symptoms of pulmonary exacerbation (Rosenfeld, M, J Pediatr 2001; 139:359-65). Patients who withdrew for the combination of predefined symptoms and need for additional antibiotics met the primary efficacy endpoint; completing their study participation.

Statistical Analyses

Efficacy and safety analyses included all randomly-assigned patients receiving ≧1 dose of AZLI/placebo. As specified in the study protocol, responses of placebo-BID and placebo-TID groups were pooled. A sample size of 210 patients for AZLI/placebo treatment was estimated as providing >90% power to detect a difference in time to antibiotic need, with α=0.05.

CFQ-R and $FEV_1$ efficacy analyses used the last observation carried forward convention. Analyses of continuous variables used Analysis of Covariance (ANCOVA) models with treatment as the fixed effect and baseline (Day 0) values as covariates. The highest aztreonam MIC at baseline was the covariant for analyzing $\log_{10}$ PA CFUs. Changes in $FEV_1$ (liters) and changes in $FEV_1\%$ predicted were analyzed using relative values; increases or decreases were calculated as percentages of the baseline $FEV_1$ or $FEV_1\%$ predicted values. Time to antibiotic need and to hospitalization were analyzed using Kaplan-Meier estimates and treatment groups compared using the log-rank test. Hospitalizations were analyzed using Wilcoxon rank-sum test (days) and Fisher's Exact test (proportion of patients). Aztreonam concentrations (Alta Analytical Laboratory, El Dorado Hills, Calif.) in plasma and sputum were summarized, as were aztreonam or tobramycin MIC values inhibiting 50% ($MIC_{50}$) or 90% ($MIC_{90}$) of PA isolates, proportion of patients with aztreonam or tobramycin MIC values above parenteral breakpoints, and the prevalence of other pathogenic bacteria (Covance Central Laboratory Services, Indianapolis, Ind.) (Gibson, R L, Am J Respir Crit. Care Med 2003; 168:918-51; Gibson, R L, Pediatr Pulmonol 2006; 41:656-65; Burns J L, Clin Infect Dis 1998; 27:158-63). Statistical Analysis Software versions 8.02 and 9.1 were used (SAS®, SAS Institute Inc, Cary, N.C.).

Results

Figure 2:
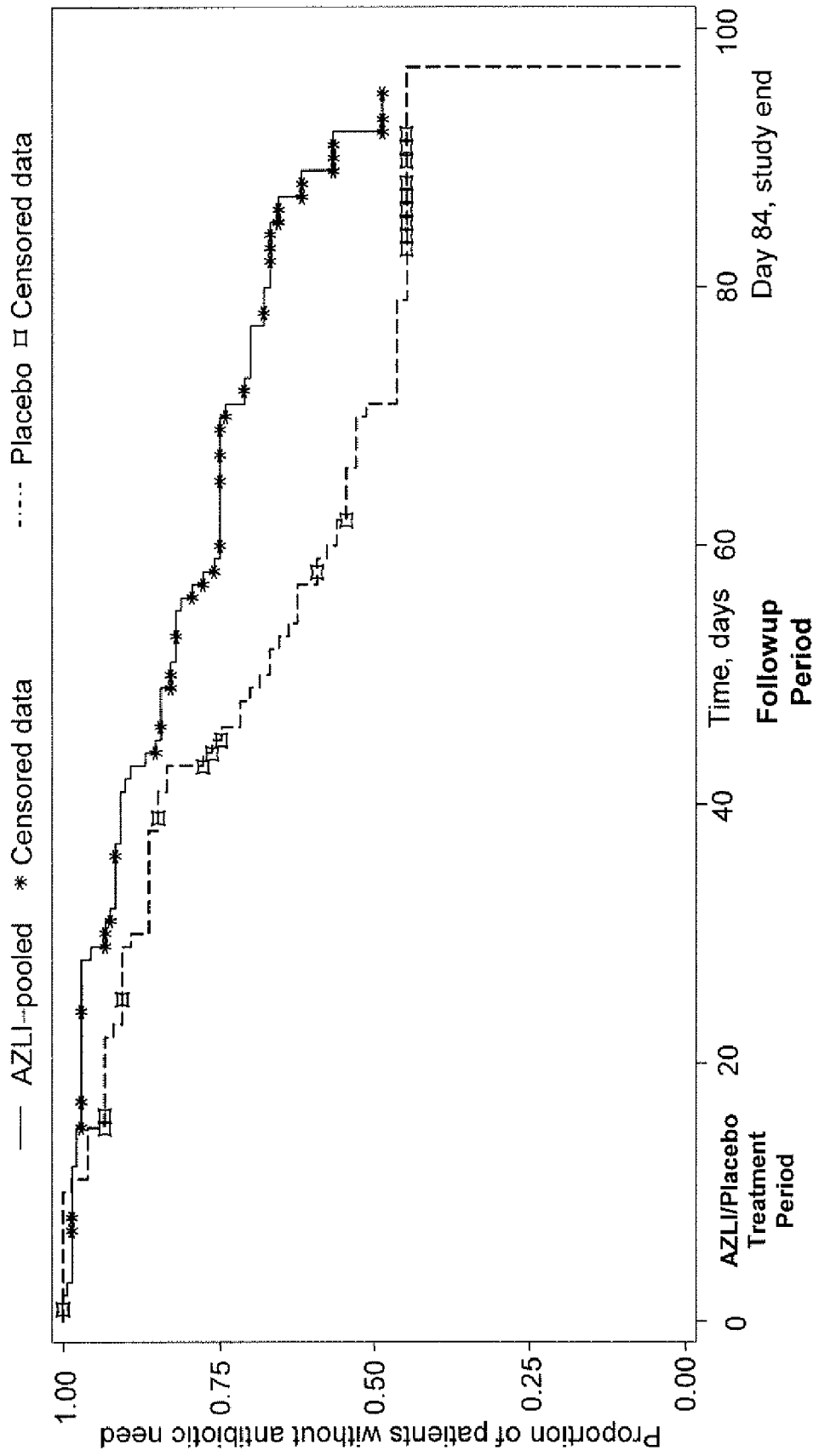
FIG. 2. Time to Need for Additional Inhaled or IV Antipseudomonal Antibiotics to Treat Symptoms Indicative of Pulmonary Exacerbation. Data were censored for patients discontinuing the study for reasons other than need for additional antibiotics to treat a predefined list of symptoms (decreased exercise tolerance, increased cough, increased sputum/chest congestion, or decreased appetite). The median time to antibiotic need is shown for both treatment groups (AZLI vs. placebo, P=0.007).

Of 363 patients screened, 211 completed the 28-day TIS run-in and began the 28-day AZLI/placebo treatment; 173 (82%) completed treatment (FIG. 1). Compliance was 99.5% during TIS run-in (≧50% doses) and 95.3% during AZLI/placebo treatment (≧66% doses). Worsening respiratory symptoms prompted most discontinuations during AZLI/placebo treatment. The majority of discontinuing patients (Days 0-84) also met the primary study endpoint, need for IV or inhaled antipseudomonal antibiotics (AZLI-BID: 17 of 32 withdrawing; AZLI-TID: 21 of 39; placebo: 38 of 50; FIGS. 1, 2).

Patient Characteristics

Patient characteristics appeared well balanced between treatment groups (Table 3). Mean age was 26.2 years, with 165 (78%) patients ≧18-years of age. Mean $FEV_1\%$ predicted was 55.1%; $FEV_1$ was ≦50% predicted value for 76 (36%) patients. Concomitant medications used at screening (>50% patients) were pancreatic enzymes (92%), salbutamol (89%), dornase alfa (85%), vitamins (84%), azithromycin (70%), and fluticasone propionate with salmeterol (56%). Average TIS use was 5.3 courses in the year before the study; 6.5 courses/year is the maximum number approved (Prescribing information, TOBI®, tobramycin inhalation solution, USP).

Efficacy

Less than half the AZLI-treated patients had required additional inhaled or IV antipseudomonal antibiotics by study end (Day 84); thus the median time to antibiotic need was greater than 84 days (FIG. 2). Data were available on use of antipseudomonal antibiotics to treat predefined respiratory symptoms occurring during the 2 weeks after study end/early withdrawal. By including these data (16 patients, added before unblinding the study), we determined the median time to antibiotic need was 21 days longer for the AZLI-pooled group than for the placebo group (92 vs 71 days, measured from baseline; P=0.007; FIG. 2). Median time to antibiotic need was also longer in the AZLI-BID (>92 days, P=0.002) and AZLI-TID (87 days, P=0.182) groups, compared with placebo (71 days).

Figure 3:
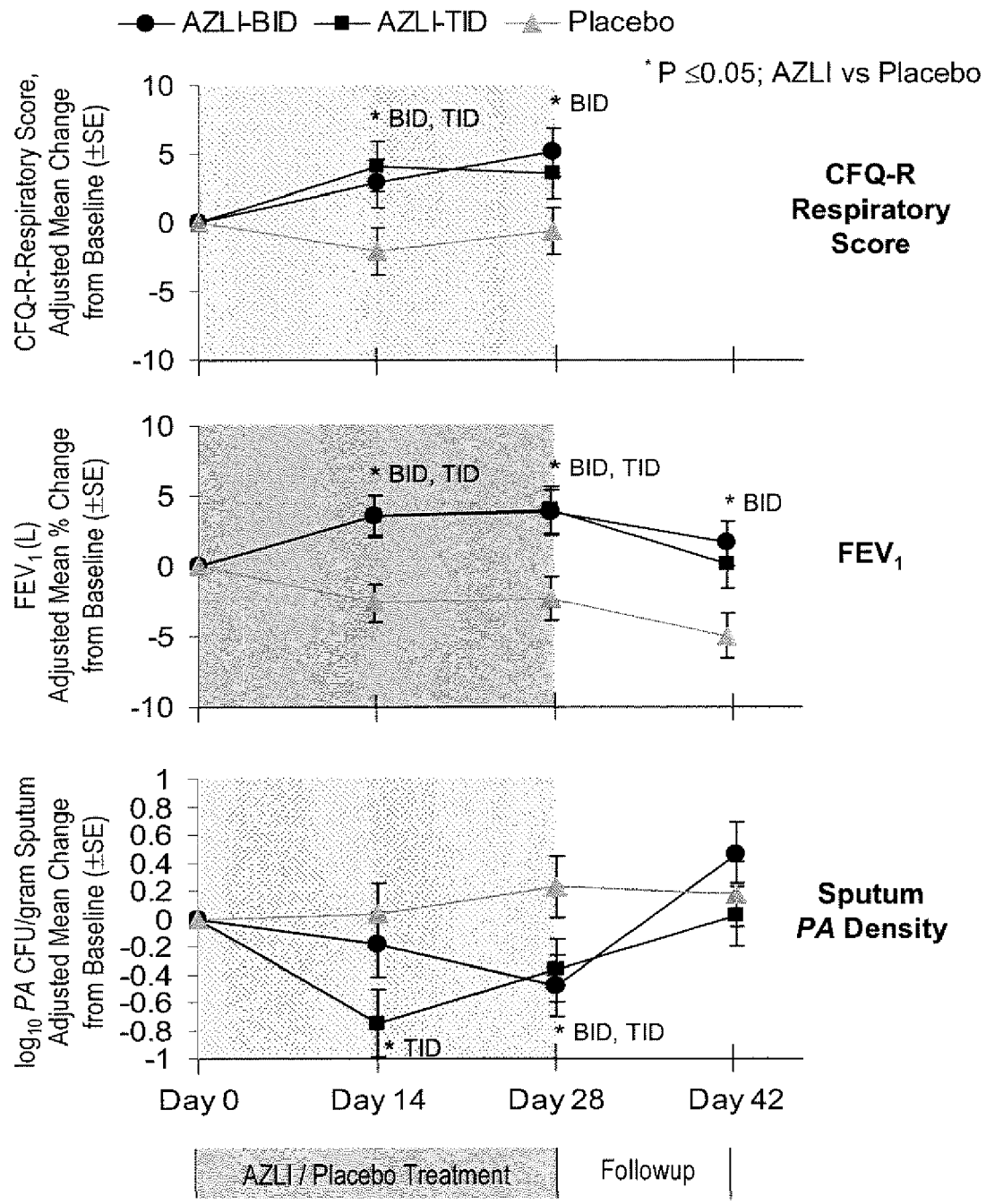
FIG. 3. Changes in Mean CFQ-R-Respiratory Scores, $FEV_1$ and PA Density in Sputum. Child, teen, and adult CFQ-R-Respiratory scores were combined. The CFQ-R was not administered on Day 42. For CFQ-R-Respiratory, at Day 28, P=0.021 for AZLI-BID vs. placebo and P=0.092 for AZLI-TID vs. placebo. For $FEV_1$ at Day 28, P=0.006 for AZLI-BID vs. placebo and P=0.005 for AZLI-TID vs. placebo. For PA Density ($\log_{10}$ PA CFU/grain sputum) at Day 28, P=0.011 for AZLI-BID vs. placebo and P=0.031 for AZLI-TID vs. placebo.

Adjusted mean CFQ-R-Respiratory scores increased 5.01 points in the AZLI-pooled group compared with placebo (Day 28, 95% confidence interval [CI]: 0.81, 9.21; P=0.020). Significant improvements were observed for both AZLI-BID and AZLI-TID groups compared with placebo (FIG. 3). Scores decreased during the followup period (Day 84; AZLI-pooled: 0.71 points; placebo: −0.78 points; change from Day 0). During AZLI/placebo treatment (Days 0-28), CFQ-R-Respiratory scores improved for more AZLI-treated than placebo-treated patients (≧5 point increase; AZLI: 52%; placebo: 37%) and worsened for fewer AZLI-treated patients (≧5 point decrease; AZLI: 28%; placebo: 38%; overall categorical comparison, P=0.029).

Figure 4:
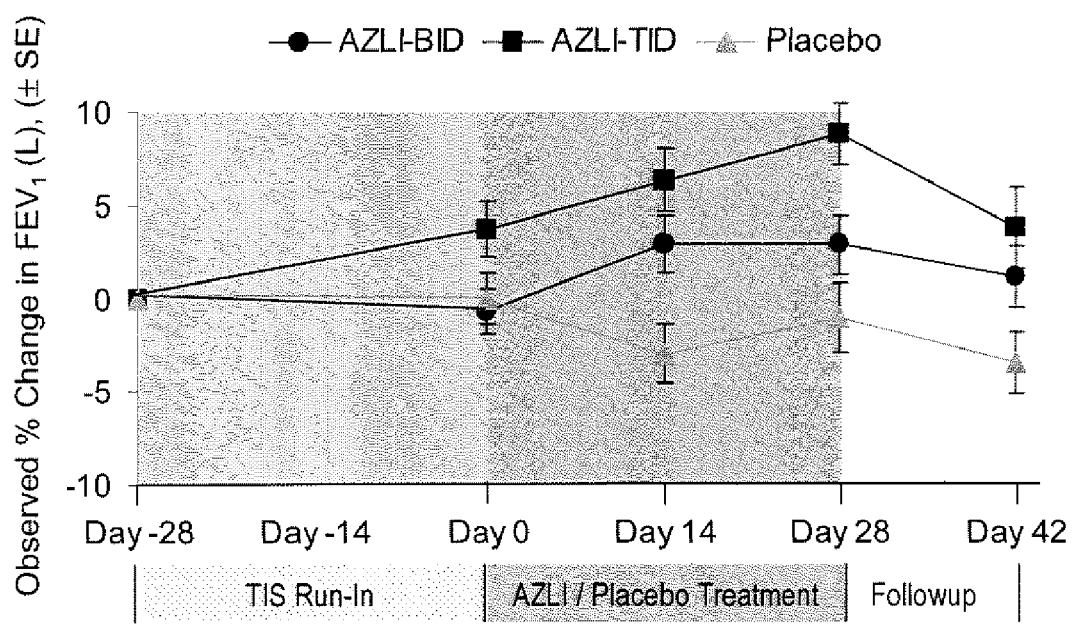
FIG. 4. Observed Percentage Change in $FEV_1$. Patients were randomly assigned to treatment groups at Day −28, and all three treatment groups received TIS during the open-label, TIS run-in period. AZLI/placebo treatment began on Day 0.

Adjusted mean $FEV_1$ improved 6.3% in the AZLI-pooled group compared with placebo (Day 28, 95% CI: 2.5, 10.1; P=0.001). Significant improvements were observed for both AZLI-BID and AZLI-TID groups compared with placebo (FIG. 3). $FEV_1$, decreased during the followup period for all groups. During both TIS run-in and AZLI treatment, improvement in observed $FEV_1$ was larger for the AZLI-TID than for the AZLI-BID group; this larger improvement was followed by a larger decline for the AZLI-TID group during the followup period (FIG. 4).

Adjusted mean $FEV_1\%$ predicted also improved in the AZLI-pooled group compared with placebo (Day 28, treatment effect=6.6%; 95% CI: 2.8, 10.4; P<0.001).

Figure 5:
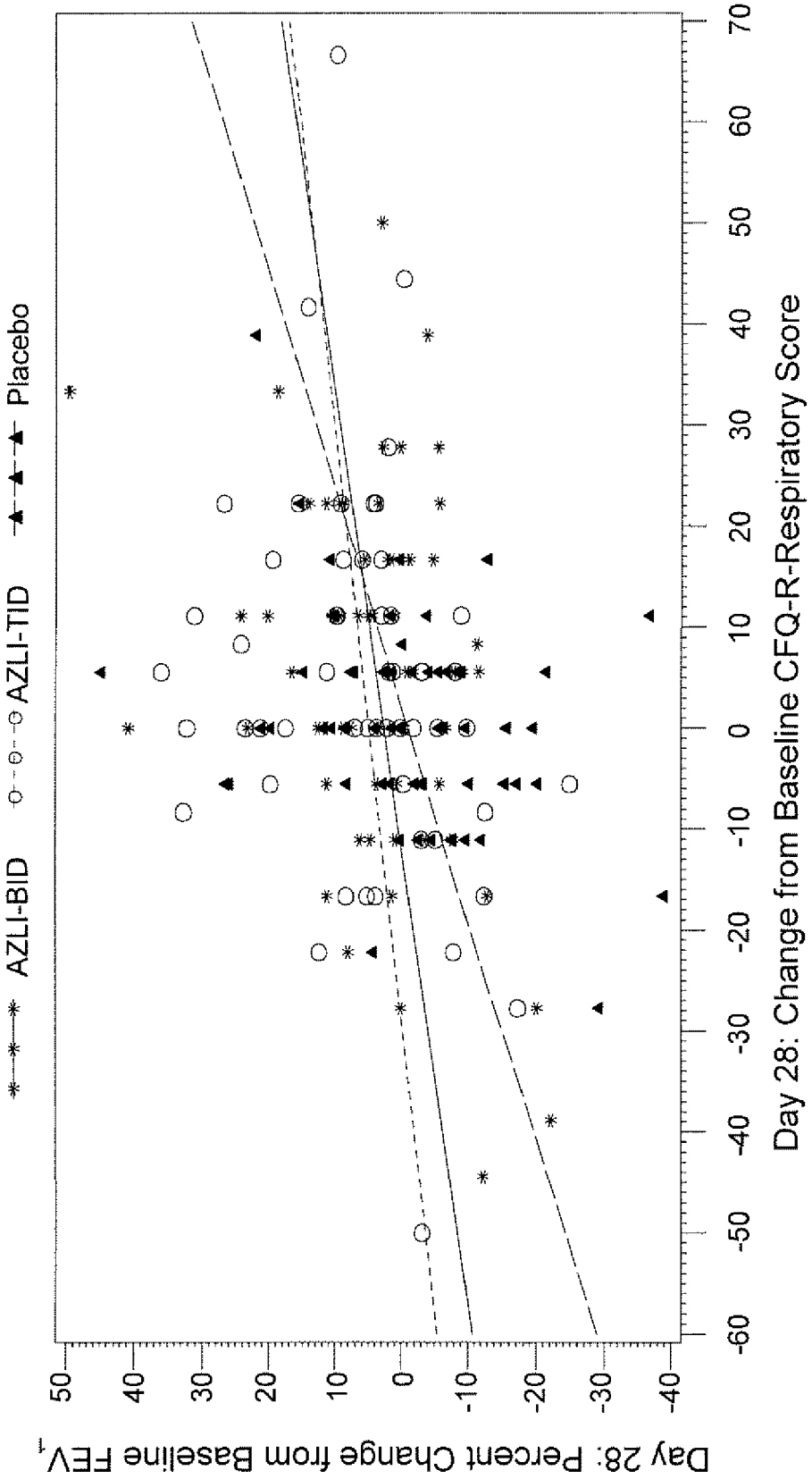
FIG. 5. Day 28 Percentage Change from Baseline $FEV_1$ vs. Day 28 Change from Baseline CFQ-R-Respiratory Scores for Individual Patients in the AZLI-BID, AZLI-TID, and Placebo Treatment Groups.

Changes in CFQ-R-Respiratory scores at end of treatment (Day 28) were modestly correlated with changes in $FEV_1$ (Pearson correlation coefficients=0.33, 0.24, 0.33; AZLI-BID, AZLI-TID, placebo; FIG. 5) and with GRCQ-Respiratory Domain responses (Pearson correlation coefficient=0.46, all groups combined, P<0.001).

Adjusted mean PA sputum density decreased 0.66 $\log_{10}$ PA CFU/gram sputum in the AZLI-pooled group compared with the placebo group (Day 28, 95% CI: −1.13, −0.19; P=0.006). Significant decreases were observed for both AZLI-BID and AZLI-TID compared with placebo (FIG. 3). PA density increased for all groups during the followup period.

During the 28-day TIS run-in, mean CFQ-R-Respiratory scores decreased −1.47, mean $FEV_1$ increased 0.9%, and mean PA density decreased 0.28 $\log_{10}$ PA CFU/gram sputum.

Time to first hospitalization and median days/number patients hospitalized did not differ significantly between treatment groups (Days 0-84). Weight increased 0.77% for the AZLI-pooled group compared with placebo (Day 28, 95% CI: 0.00, 1.55; P=0.051).

Safety

The incidence of treatment-emergent adverse events was generally comparable for the three groups (Table 4); any differences were not statistically significant. Nine patients were hospitalized because of serious adverse events occurring during the AZLI/placebo treatment period; seven for pulmonary exacerbation (AZLI-BID: 2; AZLI-TID: 4; placebo: 1) and one each for small bowel obstruction (AZLI-BID) and hyponatremia (AZLI-TID). There were no deaths during this study and no reports of anaphylaxis. Airway reactivity after treatment (acute $FEV_1$ decrease $\geq 15\%$ within 30 minutes post-treatment; Days 0, 14) occurred in 6 patients (AZLI-pooled: 4 [3.0%]; placebo: 2 [2.6%]); none of these patients withdrew for this reason.

Mean changes in vital signs and in hematology and serum chemistry variables from Day −28 or Day 0 were comparable for all treatment groups during the study. Mean total white blood cell counts, neutrophil counts, % neutrophils, and serum glucose concentrations were near or above the upper limit of normal for all treatment groups throughout the study.

Clinical Pharmacology and Microbiology

On Day 14, aztreonam concentrations in plasma 1 hour postdose were (median [range]): AZLI-BID: 581 (45-1540) ng/mL and AZLI-ID: 622 (31-1710) ng/mL and in sputum 10 minutes postdose were: AZLI-BID: 429 (0.273-3430) µg/gram and AZLI-TID: 406 (68-3240) µg/gram.

$MIC_{50}$ and $MIC_{90}$ values of aztreonam for PA remained unchanged between Days 0 and 56 except for a transient 4-fold increase on Day 14 in the AZLI-TID group. The proportion of patients having PA isolates with aztreonam MIC values >8 µg/mL (parenteral breakpoint) increased during AZLI treatment; the increase was transient in the AZLI-TID group (Day 0, 28, 42, AZLI-BID: 27%, 44%, 39%; AZLI-TID: 33%, 43%, 28%; placebo: 38%, 37%, 30%) (Gibson, R L, Am J. Respir Crit. Care Med 2003; 168:918-51). $MIC_{50}$ and $MIC_{90}$ values of tobramycin for PA isolates changed $\leq$4-fold (Days −28 to 56). The proportion of patients having PA with tobramycin MIC values $\geq$8 µg/mL (parenteral breakpoint) did not increase (Days −28 to 42). No persistent increases were observed for the prevalence of *Staphylococcus aureus, Stenotrophomonas maltophilia*, or *Achromobacter xylosoxidans* (Days 0-28); *B. cepacia* complex was not isolated.

Discussion

Inhalation of aztreonam lysine (AZLI) at a dose of 75 mg, BID or TID for 28 days, significantly delayed time to need for additional inhaled or IV antipseudomonal antibiotics to treat respiratory symptoms indicative of pulmonary exacerbation in patients with CF. Compared with placebo, AZLI treatment also significantly improved respiratory symptoms and pulmonary function and significantly decreased $\log_{10}$ PA CFUs. AZLI was well tolerated; adverse events were generally consistent with the symptoms of CF lung disease.

Although the study entry criteria were comparable, patients in this study were older (26 vs. 21 years) with higher mean $FEV_1$% predicted (55% vs. 50-51%) than patients in TIS studies a decade ago (Ramsey, B W, N. Engl. J. Med. 1999; 341:23-30). This patient population, despite being older, had less lung-disease progression; likely reflecting the improved clinical management of CF.

Patient responses during the TIS run-in period appeared markedly attenuated compared with responses observed in previous TIS studies (Ramsey, B W, N. Engl. J. Med. 1999; 341:23-30; J Moss, R B, Chest 2001; 120(Suppl):107-13S; Moss, R B, Chest 2002; 121:55-63; Ramsey, B S, N. Engl. J. Med. 1993; 328:1740-46; Smith A L, Pediatr. Pulmonol. 1989; 7:265-71; Hodson, M E, Eur Respir J. 2002; 20:658-64). Further studies will be required to elucidate the mechanism(s) underlying this apparent attenuation in clinical efficacy resulting from chronic TIS use. An increase in $FEV_1$ was observed after 28 days of AZLI treatment, therefore AZLI appears to circumvent the mechanism(s) affecting patient responses to TIS. However, this study included only one treatment period and the effectiveness of AZLI and the development of microbial resistance need to be examined over longer time periods and multiple treatment courses.

The increased CFQ-R-Respiratory scores indicated that patients perceived their respiratory symptoms as improving following AZLI treatment. CFQ-R-Respiratory scores appeared to detect change in this CF population with sensitivity equal to $FEV_1$ the established efficacy endpoint. However, these endpoints are measuring different aspects of clinical efficacy, as indicated by the modest correlation between patient-reported changes in respiratory symptoms (CFQ-R-Respiratory) and measured changes in lung function ($FEV_1$) (Goss, C H, Proc. Amer. Thorac. Soc. 2007; 4:378-86).

Patients in this study were predominantly adults (78% $\geq$ 18 years) and were extensively treated. In addition to the TIS run-in, TIS use in the previous year averaged 5.3 courses, approaching the maximum of 6.5 courses per year approved. Thus, the magnitude of improvement in $FEV_1$ (6.3%) and $FEV_1$% predicted (6.6%) following AZLI treatment was unexpected, and suggests that lung disease in adults with CF may be more responsive to additional treatment than previously believed.

Observed $FEV_1$ improved more for patients randomly assigned to the AZLI-TID group than to the AZLI-BID or placebo groups during both the TIS run-in and the AZLI/placebo treatment periods; a correspondingly larger decrease occurred during followup. Patients in the AZLI-TID group may have perceived this decrease as worsening respiratory symptoms and this may have accounted for the shorter time to antibiotic need observed for the AZLI-TID group.

The decrease in PA sputum density after AZLI treatment was small but statistically significant and was observed in clinically stable patients immediately after a course of TIS. The decrease was comparable to those observed in previous TIS studies enrolling intensively-treated patients, but smaller than those observed in previous AZLI studies enrolling less intensively-treated patients (see Clinical Trial II; Hodson, M E, Eur. Respir. J. 2002; 20:658-64; Lamb, H M, Dis. Manage. Health Outcomes 1999; 6:93-108). Thus for PA density, the magnitude of change appears dependent on recent antibiotic therapies.

The results of this study indicate that AZLI may be an effective "add-on" therapy for patients with CF and chronic PA airway infection who are intensively treated with TIS; in 2005, this group included 58% of US patients (>5 years of age) with CF and PA airway infection. The improvements in $FEV_1$ and PA sputum density decreased during the two weeks after therapy stopped. Thus, to maintain lung function, future strategies for managing patients may include rotating use of different inhaled antibiotics or use of combination therapies.

TABLE 3

Patient Demographics and Characteristics*

|  | Placebo n = 76 | AZLI-BID n = 69 | AZLI-TID n = 66 | AZLI-Pooled n = 135 |
|---|---|---|---|---|
| Age, years; mean (range) | 27.9 (10-65) | 26.5 (10-50) | 24.1 (7-50) | 25.3 (7-50) |
| Age <18 years; n (%) | 12 (15.8%) | 17 (24.6%) | 17 (25.8%) | 34 (25.2%) |
| Male; n (%) | 45 (59.2%) | 38 (55.1%) | 38 (57.6%) | 76 (56.3%) |
| TIS courses in previous year; mean | 5.26 | 5.46 | 5.26 | 5.36 |
| CFTR Genotype; n (%) | | | | |
| Homozygous for ΔF508 | 34 (45%) | 25 (36%) | 31 (47%) | 56 (41%) |
| Heterozygous for ΔF508 | 20 (26%) | 15 (22%) | 12 (18%) | 27 (20%) |
| Unidentified or Other | 22 (29%) | 29 (42%) | 23 (35%) | 52 (39%) |
| Dornase Alfa use; % patients | 89.5% | 81.2% | 84.8% | 83.0% |
| Azithromycin use; % patients | 65.8% | 69.6% | 74.2% | 71.9% |
| MIC of tobramycin for all PA isolates, μg/mL | | | | |
| $MIC_{50}$ | 2 | 1 | 2 | 1 |
| $MIC_{90}$ | 256 | 16 | 64 | 32 |
| Number of isolates tested | 137 | 104 | 107 | 211 |
| $FEV_1$ % predicted; mean (SD) | 53.9 (15.3) | 56.3 (14.8) | 55.4 (16.3) | 55.8 (15.5) |
| Patients with $FEV_1 \leq 50\%$ predicted value, n (%) | 30 (39.5%) | 24 (35.3%) | 22 (33.3%) | 46 (34.3%) |
| CFQ-R-Respiratory score; mean (SD) | 62.1 (19.7) | 63.1 (16.7) | 64.2 (18.1) | 63.7 (17.4) |
| MIC of aztreonam for all PA isolates, μg/mL | | | | |
| $MIC_{50}$ | ≤1 | 2 | 2 | 2 |
| $MIC_{90}$ | 64 | 64 | 32 | 32 |
| Minimum MIC | ≤1 | ≤1 | ≤1 | ≤1 |
| Maximum MIC | 1024 | >2048 | 1024 | >2048 |
| Number of isolates tested | 125 | 105 | 111 | 216 |

*Age and concomitant medications measured at screening; $FEV_1$% predicted and MIC of tobramycin for PA measured at Day −28; CFQ-R-Respiratory scores and MIC of aztreonam for PA measured at Day 0. There were no statistically significant differences in demographic or baseline characteristics between the AZLI and placebo groups

TABLE 4

Treatment-Emergent Adverse Events (TEAEs) ≥5.0% in any Treatment Group during the ALZI/placebo Treatment Period.

| TEAEs ≥5% in any treatment group*, n (%) | Placebo n = 76 | AZLI-BID n = 69 | AZLI-TID n = 66 | AZLI-Pooled n = 135 |
|---|---|---|---|---|
| Cough | 26 (34.2) | 19 (27.5) | 24 (36.4) | 43 (31.9) |
| Productive Cough | 13 (17.1) | 9 (13.0) | 9 (13.6) | 18 (13.3) |
| Wheezing | 6 (7.9) | 5 (7.2) | 9 (13.6) | 14 (10.4) |
| Haemoptysis | 7 (9.2) | 7 (10.1) | 6 (9.1) | 13 (9.6) |
| Nasal Congestion | 6 (7.9) | 5 (7.2) | 5 (7.6) | 10 (7.4) |
| Rhinorrhoea | 2 (2.6) | 5 (7.2) | 5 (7.6) | 10 (7.4) |
| Headache | 5 (6.6) | 2 (2.9) | 6 (9.1) | 8 (5.9) |
| Pharyngolaryngeal Pain | 7 (9.2) | 3 (4.3) | 5 (7.6) | 8 (5.9) |
| Dyspnoea | 3 (3.9) | 2 (2.9) | 5 (7.6) | 7 (5.2) |
| Pyrexia | 2 (2.6) | 4 (5.8) | 3 (4.5) | 7 (5.2) |
| Respiratory Tract Congestion | 5 (6.6) | 5 (7.2) | 2 (3.0) | 7 (5.2) |
| Abdominal Pain, Upper | 3 (3.9) | 4 (5.8) | 1 (1.5) | 5 (3.7) |
| Decreased Appetite | 5 (6.6) | 4 (5.8) | 1 (1.5) | 5 (3.7) |
| Fatigue | 7 (9.2) | 3 (4.3) | 2 (3.0) | 5 (3.7) |
| Dysphonia | 4 (5.3) | 1 (1.4) | 1 (1.5) | 2 (1.5) |
| Exercise Tolerance Decreased | 4 (5.3) | 1 (1.4) | 1 (1.5) | 2 (1.5) |
| Sinus Congestion | 5 (5.6) | 0 (0.0) | 2 (3.0) | 2 (1.5) |

*TEAEs coded using the Medical Dictionary for Regulatory Activities (MedDRA) preferred term; for TEAEs with incidence ≧10% in any group, % patients for each TEAE did not differ significantly between treatment groups (Fisher's Exact test).

Clinical Trial II

The study described herein assessed the efficacy and safety of AZLI 75 mg, administered three times daily for 28 days to patients with moderate to severe CF lung disease and PA airway infection. The primary efficacy endpoint was change in clinical symptoms, measured with the CF Questionnaire-Revised Respiratory Scale (CFQ-R-Respiratory). This study focused on patients with CF who had not been intensively treated with TIS during the previous year and were not being treated with azithromycin at study entry.

Methods

Study Design

Figure 6:
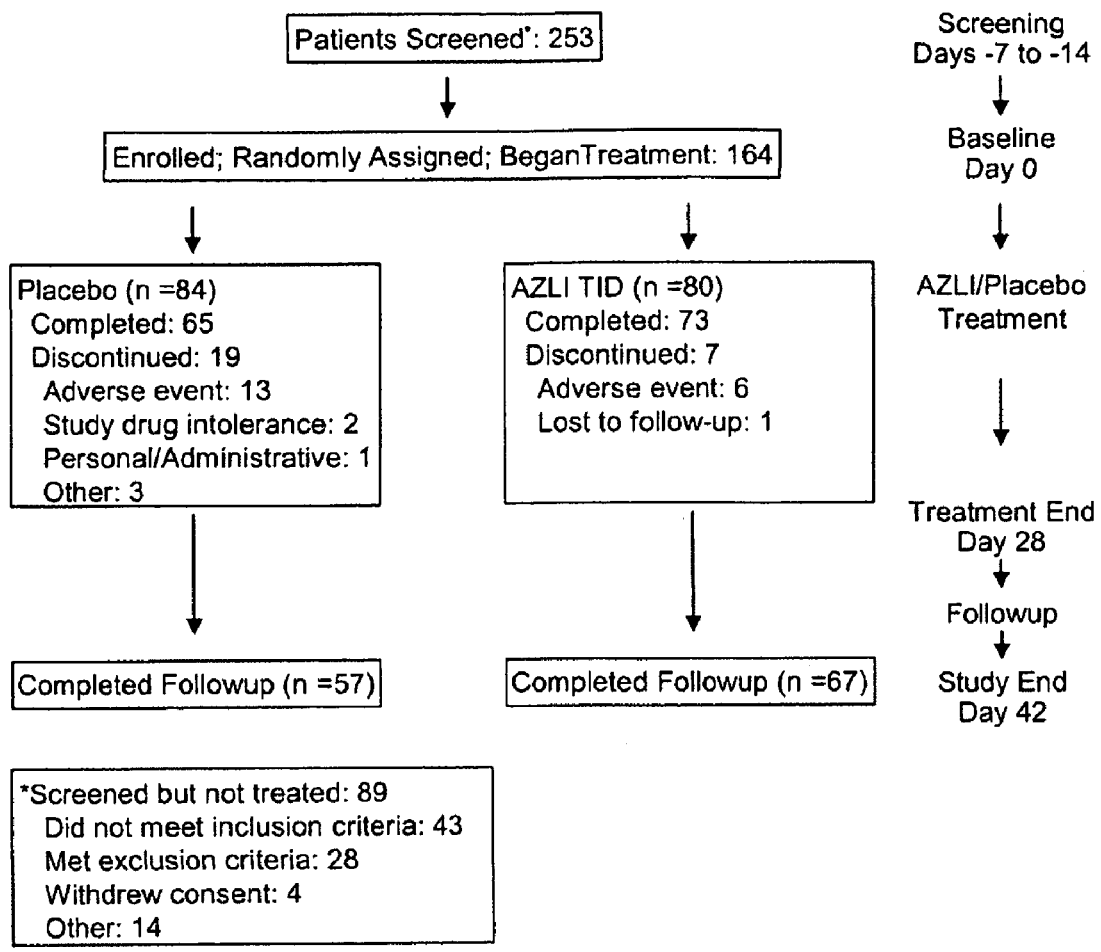
FIG. 6. Study Design and Patient Disposition for Clinical Trial II.

This randomized, double-blind, placebo-controlled, study was conducted at 53 CF centers in the US, Canada, Australia, and New Zealand (June, 2005-April, 2007). At baseline (Day 0), eligible patients were stratified by CF disease severity using $FEV_1$% predicted (moderate: $FEV_1$>50% to ≦75% predicted; severe: $FEV_1 \geq 25\%$ to $\leq 50\%$ predicted; measured at screening [between Days −14 and −7]), and randomly assigned to 28-days treatment with 75 mg AZLI or placebo (1:1; three times daily). Patients were monitored mid-treatment (Day 14), at treatment end (Day 28), and 14 days after completing treatment (Day 42; FIG. 6).

A physical exam was performed at screening. Spirometry (American Thoracic Society standards, Am J. Respir. Crit. Care Med. 1995; 152:1107-36) was performed at every study visit (before and 30 minutes after any treatment). $FEV_1\%$ predicted values were calculated using the Knudson equation.

AZLI (75 mg aztreonam, 52.5 mg lysine monohydrate) or placebo (5 mg lactose), diluted in 1 mL 0.17% NaCl, were administered with the eFlow® Electronic Nebulizer (PARI Innovative Manufacturers, Midlothian, Va.). Patients self-administered a short-acting β2-agonist 15 minutes before the first spirometry measurements at study visits and self-administered a β2-agonist before study medication at home (within 2 hours before dosing for short-acting or 30 minutes to 8 hours before dosing for long-acting agents). Patients continued any prescribed bronchodilator use, excluding a 4 hour period before study visits.

Study medication was dispensed at baseline; used/unused vials were subsequently collected to assess treatment compliance.

This study was conducted in compliance with the Declaration of Helsinki, the International Conference on Harmonisation guideline for Good Clinical Practices, and the applicable regulations for each participating country. Institutional Review Boards (U.S.) and Ethics Committees (Canada, Australia, New Zealand) approved the study for each site, and all patients or their guardians provided written informed consent prior to any study procedures. The ClinicalTrials.gov accession number is NCT00112359.

Study Population

Eligible patients were $\geq 6$ years of age with a documented diagnosis of CF and moderate to severe lung disease ($FEV_1 \geq 25\%$ to $\leq 75\%$ predicted), arterial oxygen saturation $\geq 90\%$ on room air (at screening), the ability to perform reproducible pulmonary function tests, and PA airway infection (documented at screening or twice within previous year, including once within previous 3 months).

Exclusion criteria included recent (Day −28 to screening) inhaled, intravenous, or oral administration of antipseudomonal antibiotics or azithromycin; recent aerosolized hypertonic saline use (except for sputum induction); current oral corticosteroid use equivalent to >10 ing prednisone daily; airway cultures yielding *Burkholderia cepacia* complex during previous 2 years; daily continuous oxygen supplementation or >2 L/minute at night; local or systemic hypersensitivity to monobactam antibiotics; intolerance to inhaled short-acting β2-agonists; recent (since 7 days before screening) changes in antimicrobial, bronchodilator, anti-inflammatory, corticosteroid medications or physiotherapy technique/schedule; lung transplantation; new findings on chest radiograph at screening or within previous 90 days; AST or ALT >5-times, or serum creatinine >2-times upper limit of normal (at screening); pregnancy; lactation; or, in the opinion of the investigator, medical or psychiatric illness interfering with study participation.

Efficacy Measures

CFQ-R was administered at baseline and every study visit thereafter. Unless noted differently, responses to adult, teen, and child versions were combined for presentation (Quittner, A L, Chest 2005; 128:2347-54). The primary efficacy endpoint was change in clinical symptoms, assessed with CFQ-R-Respiratory scores. Scores ranged from 0 to 100; increasing scores indicated improvement. In an earlier study, the minimal clinically important difference (MCID) score for the CFQ-R-Respiratory Scale was identified as five (Guyatt, G H, Med. Care 2000; II:175-9; Jaeschke, R, Control Clin. Trials 1989; 10:407-15). Thus, a five point difference in CFQ-R-Respiratory scores indicated improving/worsening symptoms.

Secondary efficacy endpoints included changes in pulmonary function, hospitalizations, and non-respiratory CFQ-R Scales.

Microbiological endpoints included change in sputum PA density (colony forming units (CFU)/gram sputum, $log_{10}$ transformed), the minimum inhibitory concentration (MIC) of aztreonam for PA, number of isolates and proportion of patients with aztreonam MIC >8 μg/ml for PA (parenteral breakpoint), and the prevalence of other pathogens.

Safety Measures

Adverse events and changes in clinical laboratory values, vital signs, and airway reactivity were monitored. Worsening CF symptoms were treated as adverse events. Patients requiring non-study antipseudomonal antibiotics were withdrawn from the study.

Statistical Analyses

Efficacy and safety analyses included all randomly-assigned patients receiving $\geq 1$ dose of AZLI/placebo. $FEV_1$ and CFQ-R analyses used the last observation carried forward convention. A sample size of 140 was estimated to provide 77% power to detect an 8-point difference for change in CFQ-R-Respiratory scores (assuming SD=20) and to provide >90% power to detect a 9% difference in $FEV_1$ (assuming SD=12), with α=0.05.

Continuous variables were analyzed using Analysis of Covariance (ANCOVA) models with treatment as the fixed effect; disease severity (moderate/severe) and baseline values (except for analysis of $log_{10}$ PA CFUs in sputum) were covariates. Changes in $FEV_1$ (liters) and changes in $FEV_1\%$ predicted were analyzed using relative values; increases/decreases were calculated as percentages of the baseline $FEV_1$ or $FEV_1\%$ predicted values.

At Day 28, patients were categorized as improved ($\geq 5$ point increase from baseline CFQ-R-Respiratory scores), worse ($\geq 5$ point decrease from baseline) or stable/no change (<5 point change from baseline). These categories were analyzed with the Cochran-Mantel-Haenszel mean score statistic with disease severity and baseline score as stratification variables Hospitalizations were analyzed using Wilcoxon rank-sum test (days) and Fisher's Exact test (proportion of patients). Aztreonam concentrations inhibiting the growth of 50% ($MIC_{50}$) or 90% ($MIC_{90}$) PA isolates and the presence of other pathogenic bacteria were summarized (Covance Central Laboratory Services, Indianapolis, Ind.) as were plasma and sputum aztreonam concentrations (Alta Analytical Laboratory, El Dorado Hills, Calif.) (Burns, J L, Clin. Infect. Dis. 1998; 27:158-63). Statistical analyses were performed using Statistical Analysis Software versions 8.02 and 9.1 (SAS®, SAS Institute Inc, Cary, N.C.).

Results

Of 253 patients screened, 164 began treatment with AZLI or placebo, 138 completed 28-days treatment, and 124 completed the study (FIG. 6). Compliance with dosing ($\geq 80\%$ doses) was 92%. The most common reason for discontinuation during the 28-day treatment was adverse event (ALZI: 6, 7.5%; placebo: 13, 15.5%; FIG. 6); most of these patients (16/19) required treatment with non-study antipseudomonal antibiotics.

Patient Characteristics

Overall demographic characteristics appeared well balanced between treatment groups (Table 5). Mean age was 29.6 years. Most patients (127, 77.4%) were ≧18 years of age. About half (93, 56.7%) were male (Table 5).

At screening, 60 (36.6%) patients had $FEV_1$≦50% predicted values and at baseline, mean $FEV_1$% predicted was 54.6%. Concomitant medications used by ≧40% patients at baseline included pancreatic enzymes (87%), vitamins (87%), salbutamol (79%), dornase alfa (65%), and fluticasone propionate with salmeterol xinafoate (40%).

Efficacy

Figure 7:
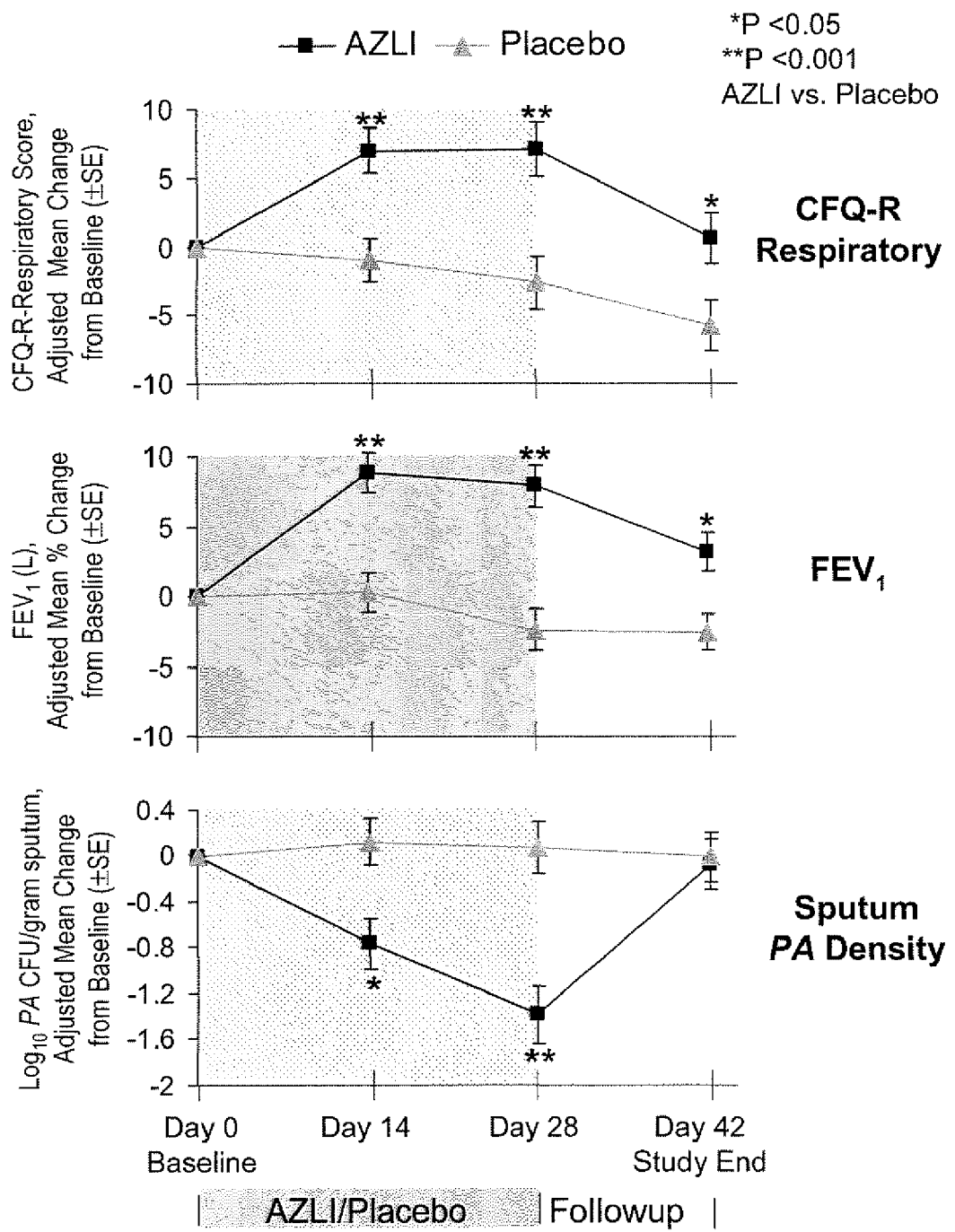
FIG. 7. Adjusted Mean CFQ-R-Respiratory Scores, $FEV_1$ and Sputum PA Density: Change from Baseline to Study End (Days 0-42). Child, teen, and adult responses were combined for CFQ-R-Respiratory scores.

Adjusted mean CFQ-R-Respiratory scores increased from baseline values for AZLI-treated patients and decreased for placebo-treated patients (Day 28, treatment difference=9.7 points; 95% Confidence interval [CI]=4.3, 15.1; P<0.001; FIG. 7, Table 6). By Day 42 (14 days after treatment ended), scores had declined but remained above baseline values for AZLI-treated patients, and had continued to decline for placebo-treated patients (Day 42, treatment difference=6.3 points; 95% CI=1.2, 11.4; P=0.015; FIG. 7).

Figure 8:
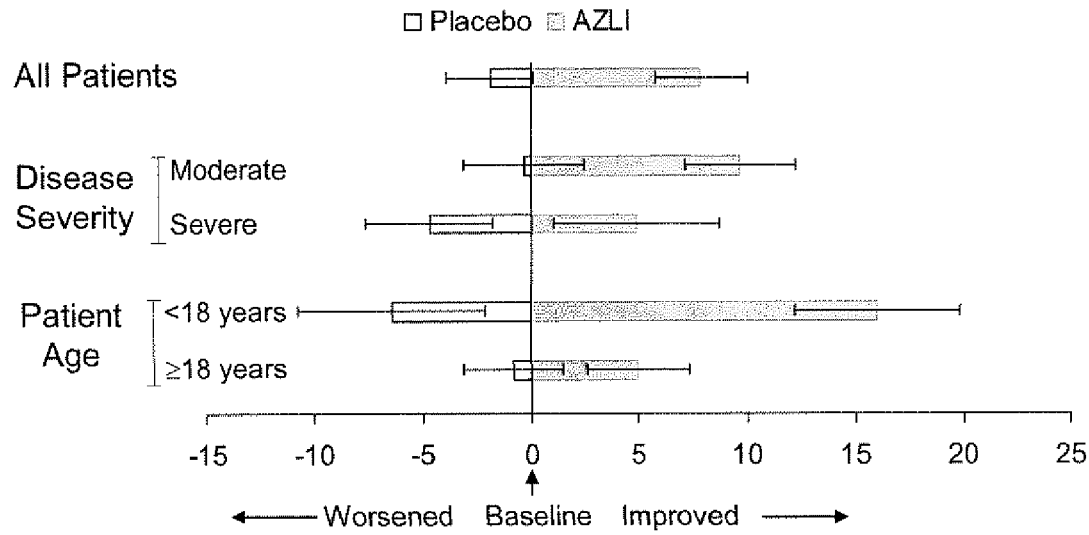
FIG. 8. Change from Baseline to End of Treatment for CFQ-R-Respiratory Scores and $FEV_1$: Effects of Age and Baseline CF Lung Disease Severity. The number of patients included in analyses: all patients: AZLI, 80; placebo, 83/84; disease severity-moderate: AZLI, 50; placebo, 53/54; disease severity-severe: AZLI, 30; placebo, 30; age <18 years: AZLI, 21; placebo, 16; age ≧18 years: AZLI, 59; placebo, 67/68.
Figure 8:
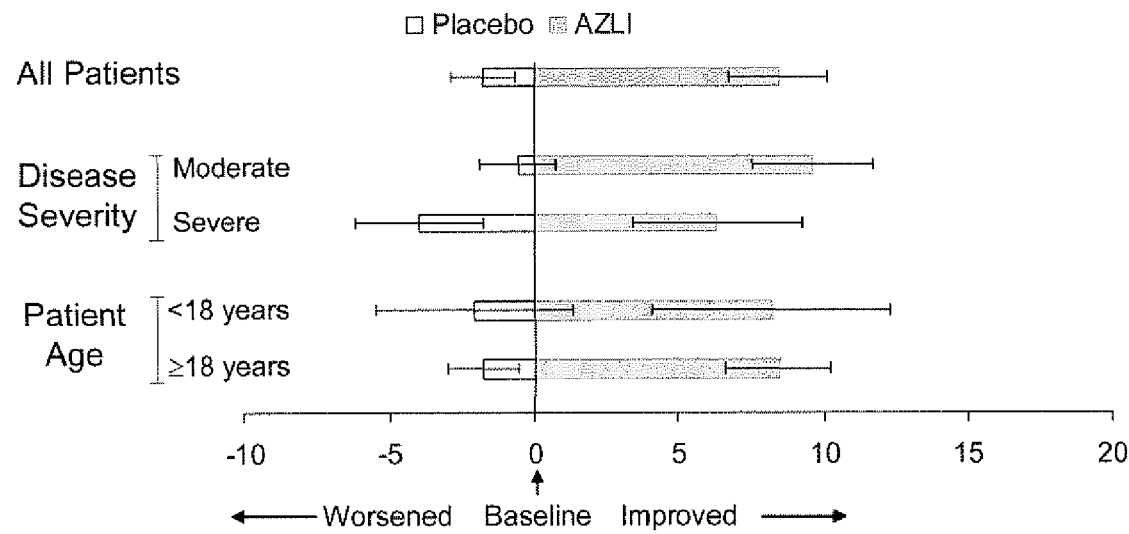

Compared with placebo, mean CFQ-R-Respiratory scores increased for AZLI-treated patients with differing CF lung disease severity and ages (FIG. 8). Treatment responses were comparable for patients with moderate or severe lung disease and were larger for younger patients (<18 years) than for older patients.

During treatment, CFQ-R-Respiratory scores improved for more AZLI-treated patients than placebo-treated patients (≧5 point increase; AZLI: 45, 56%; placebo: 31, 37%). Scores also worsened for fewer AZLI-treated patients (≧5 point decrease; AZLI: 20, 25%; placebo: 37, 45%; P=0.006 for overall categorical comparison).

Adjusted mean $FEV_1$ increased from baseline values for AZLI-treated patients and decreased for placebo-treated patients (Day 28, treatment difference=10.3%; 95% CI=6.3, 14.3; P<0.001; FIG. 7). By Day 42 (14 days after treatment ended), mean $FEV_1$ had declined but remained above baseline for AZLI-treated patients, and had continued to decline for placebo-treated patients (Day 42, treatment difference=5.7%; 95% CI=2.1, 9.4; P=0.002). Compared with placebo, AZLI treatment improved mean $FEV_1$ values for patients with differing CF lung disease severity and ages. Treatment responses were comparable for the different subgroups (FIG. 8).

At treatment end, changes in CFQ-R-Respiratory scores and in $FEV_1$ were modestly correlated (Day 28, Pearson correlation coefficients; AZLI: 0.32; placebo: 0.32).

Adjusted mean $FEV_1$% predicted also increased for AZLI-treated patients and decreased for placebo treated patients during treatment (Day 28, treatment difference=10.2%; 95% CI=6.2, 14.2; P<0.001) and declined for both groups after treatment (Day 42, treatment difference=5.7%; 95% CI=2.0, 9.4; P=0.003).

Adjusted mean sputum PA density decreased for AZLI-treated patients and remained near baseline for placebo-treated patients (Day 28, treatment difference=-1.453 $\log_{10}$ CFU/gram; 95% CI=-2.1, -0.8; P<0.001; FIG. 7). Values at Day 42 (14 days after treatment ended) were near baseline values for both treatment groups (P=0.822).

There was a trend towards fewer patients being hospitalized in the AZLI group (5%) than in the placebo group (14%; Days 0-42; P=0.064) and towards fewer hospitalization days (AZLI: 0.5 days; Placebo: 1.5 days; P=0.049). Compared with placebo, weight increased 1.0% (Day 28, 95% CI: 0.33, 1.69; P=0.004) for the AZLI-treated group.

Responses of AZLI-treated patients were significantly larger than those of placebo-treated patients for six of the eleven non-respiratory CFQ-R Scales; these included Eating, Emotional Functioning, Health Perceptions, Physical Functioning, Role/School, and Vitality (Table 6).

Safety

The incidence of treatment-emergent adverse events was similar for both groups during the AZLI/placebo treatment period, except productive cough was reported by significantly fewer AZLI-treated (10, 12.5%) than placebo-treated patients (21, 25%; P=0.047; Table 7). Five patients were hospitalized during the AZLI/placebo treatment period; two for respiratory symptoms (AZLI: 1; placebo: 1), two for bowel obstruction (AZLI: 1, placebo: 1) and one for umbilical hernia (placebo). Airway reactivity, defined as ≧15% decrease in $FEV_1$ within 30 minutes after AZLI/placebo dosing at study visits, occurred in 8 patients (AZLI: 3; placebo: 5); none of these patients withdrew for this reason. No clinically significant changes in vital signs or mean clinical laboratory values were observed except a trend in AZLI-treated patients; during the AZLI/placebo treatment period, they had fewer shifts above reference ranges than placebo-treated patients for white blood cell, platelet, and neutrophil counts and neutrophil percent, all markers of systemic inflammation. There were no deaths during this study and no reports of anaphylaxis.

Clinical Pharmacology and Microbiology

Sputum aztreonam concentrations 10 minutes postdose were (median [range]): 530 (8-6010), 677 (2-2780), and 451 (0.6-2800) μg/g sputum on Days 0, 14, and 28. Plasma aztreonam concentrations 1 hour postdose were (median [range]): 495 (0-1620), 595 (12-1660), and 603 (0-1740) ng/mL on Days 0, 14, and 28.

Throughout the study, $MIC_{50}$ and $MIC_{90}$ values of aztreonam for all PA isolates from placebo-treated patients remained unchanged or decreased. PA isolates from AZLI-treated patients displayed a transient 4-fold increase in $MIC_{90}$ (Day 14). The number of PA isolates with aztreonam MIC >8 μg/mL (parenteral breakpoint) and the proportion of patients with such isolates did not increase during AZLI treatment. There was no evidence for persistent increases in *Stenotrophomonas maltophilia, Staphylococcus aureus* or *Achromobacter xylosoxidans*; *B. cepacia* complex was not isolated.

Discussion

Inhaled aztreonam lysine (AZLI), administered at a dose of 75 mg three times daily for 28 days to patients with moderate to severe CF lung disease and PA airway infection, significantly improved respiratory symptoms and pulmonary function and significantly decreased sputum PA density, compared with placebo. AZLI was well tolerated; adverse events were generally consistent with symptoms of CF lung disease.

This was the first aerosolized-antibiotic clinical study to use a patient-reported outcome (CFQ-R-Respiratory) as the primary efficacy endpoint, although a recent study of hypertonic saline used it as a secondary endpoint (Elkins, M R, N. Eng. J. Med. 2006; 354:229-40; Donaldson, S H, N. Engl. J. Med. 2006; 354:241-50). CFQ-R-Respiratory scores directly measured the benefits of AZLI from the patient's perspective (Quittner, A L, Chest 2005; 128:2347-54, Goss, C H, Proc. Amer. Thorac. Soc. 2007; 4:378-86). The improvement reported for respiratory symptoms was confirmed by significant improvements in $FEV_1$ and by an adverse event measure: compared with placebo, AZLI treatment decreased by half the reports of the adverse event, "productive cough." These results demonstrate that patients with CF can reliably report their symptoms using a standardized measure, and provides support for the use of patient-reported outcomes in clinical studies. However, the modest correlation between patient-reported changes in respiratory symptoms (CFQ-R-Respiratory) and measured changes in lung function ($FEV_1$) suggests they are measuring different aspects of clinical efficacy; thus a combination of patient-reported and physiological measurements may be optimal.

In addition to respiratory symptoms, AZLI-treated patients reported improvements in disease-related symptoms involving eating, emotional and physical functioning, health perceptions, role/school functioning, and vitality. These results have particular relevance for patients with a chronic illness, who must adhere to complex, time-consuming medical regimens that affect their normal activities. Their perception of treatment benefit is likely to improve adherence to treatment regimens and influence their long-term health outcomes (Modi, A C, Pediatr Pulmonol. 2005; S28:371).

CFQ-R-Respiratory scores and $FEV_1$ increased for AZLI-treated patients from baseline to mid-treatment (Days 0-14), with little additional change to treatment end (Day 28). However, treatment effects continued to be observed at Day 42, 14 days after treatment ended. Adjusted mean PA density decreased throughout the 28-day AZLI treatment and returned to baseline values at Day 42.

Compared with patients in the AZLI study described in Clinical Trial I, fewer patients in this study used dornase alfa (65% vs. 85% patients), TIS (1.8 vs. 5.3 mean courses in previous year), and azithromycin (0% vs. 70% patients; excluded by study entry criteria). Patients in both AZLI studies had comparable lung function ($FEV_1 \geq 25\%$ to $\leq 75\%$ predicted values). This less-intensive treatment regimen may reflect a number of factors: patient intolerance to available therapies, lack of clinical response to specific therapies, clinician and patient preferences, or the difficulty of obtaining TIS in some countries participating in the study. The treatment effects observed for these less intensively-treated patients (9.7 point increase for CFQ-R-Respiratory, 10.3% increase for $FEV_1$, 10.2% increase for $FEV_1\%$ predicted, 1.453 $\log_{10}$ decrease in sputum PA density) were larger than those observed in the AZLI study described in the accompanying paper (5.0 point increase for CFQ-R-Respiratory, 6.3% increase for $FEV_1$, 6.6% increase for $FEV_1\%$ predicted, 0.66 $\log_{10}$ decrease in sputum PA density) and approached the treatment effects observed in the original TIS studies a decade ago (approximately 12% increase for $FEV_1\%$ predicted) (Ramsey, B W, N. Engl. J. Med. 1999; 341:23-30; Lamb, H M, Dis Manage Health Outcomes 1999; 6:93-108).

AZLI may provide an important new therapy for patients with CF who have moderate to severe lung disease. Further studies will be needed to define the appropriate strategy for incorporating AZLI use into the treatment of chronic PA airway infection.

TABLE 5

Patient Demographics and Baseline Characteristics*

|  | Placebo n = 84 | AZLI n = 80 |
|---|---|---|
| Country; n (%) | | |
| US and Canada | 63 (75.0) | 62 (77.5) |
| Australia and New Zealand | 21 (25.0) | 18 (22.5) |
| Age, years*; mean (range)† | 31.7 (11-74) | 27.4 (7-54) |
| Age group; n (%) | | |
| <18 years | 16 (19.0) | 21 (26.3) |
| ≧18 years | 68 (81.0) | 59 (73.8) |
| Male; n (%) | 45 (53.6) | 48 (60.0) |
| Weight, kg; mean (SD) | 60.7 (15.2) | 59.9 (17.3) |
| Body Mass Index, kg/m²; mean (SD) | 21.9 (3.9) | 21.4 (4.3) |
| CFTR Genotype; n (%) | | |
| Homozygous for ΔF508 | 30 (35.7) | 38 (47.5) |
| Heterozygous for ΔF508 | 22 (26.2) | 21 (26.3) |
| Unidentified or Other | 32 (38.1) | 21 (26.3) |
| TIS courses** in previous year; mean | 1.7 | 1.8 |
| Dornase Alfa use; % patients | 64% | 66% |
| $FEV_1$ % of predicted value; mean (SD) | 54.8 (14.0) | 54.4 (13.4) |
| Patients with $FEV_1 \leq 50\%$ predicted value*, n (%) | 30 (35.7) | 30 (37.5) |
| CFQ-R-Respiratory score; mean (SD) | 60.9 (18.9) | 60.5 (18.1) |
| MIC of aztreonam for all PA isolates, μg/mL | | |
| $MIC_{50}$ | 2 | 4 |
| $MIC_{90}$ | 64 | 128 |
| Minimum MIC | ≦1 | ≦1 |
| Maximum MIC | 256 | >2048 |
| Number of isolates tested | 140 | 128 |

*At screening (Between Days −7 and −14)
**TIS is not commercially available in Australia and New Zealand. Two patients from these countries reported TIS use during the previous year.
†The only significant difference (P < 0.05) in demographic or baseline characteristics between the two groups was in mean age, with patients in the AZLI group being younger. However, the proportion of patients categorized as <18 versus ≧18 years of age was not significantly different between the AZLI and placebo groups.

TABLE 6

CFQ-R Scales: Change in Score from Baseline to End of Treatment (Days 0-28)

| CFQ-R Scales | Change from Baseline, Adjusted Mean Score | | 95% Confidence Intervals | P values |
|---|---|---|---|---|
| | Placebo | AZLI | | |
| Body Image | 1.0 | 3.2 | −2.2, 6.5 | 0.327 |
| Digestion | 1.9 | 2.2 | −3.5, 4.0 | 0.889 |
| Eating | −4.7 | 3.6 | 4.1, 12.7 | <0.001 |
| Emotional Functioning | −1.3 | 3.9 | 1.6, 8.8 | 0.005 |
| Health Perceptions | −4.8 | 5.0 | 4.8, 14.9 | <0.001 |
| Physical Functioning | −6.9 | 2.3 | 3.6, 14.8 | 0.001 |
| Respiratory Symptoms | −2.6 | 7.1 | 4.3, 15.1 | <0.001 |
| Role/School | −4.2 | 2.1 | 1.3, 11.4 | 0.014 |
| Social Functioning | −3.6 | −1.2 | −1.7, 6.5 | 0.248 |
| Treatment Burden | −3.1 | 0.2 | −1.5, 7.9 | 0.177 |
| Vitality | −4.4 | 3.6 | 2.5, 13.5 | 0.005 |
| Weight | 1.4 | 4.7 | −4.0, 10.5 | 0.376 |

TABLE 7

Treatment-Emergent Adverse Events (TEAEs) Reported by ≧5% Patients in Either Treatment Group during the AZLI/placebo Treatment Period

| TEAEs*, n (%) | Placebo n = 84 | AZLI n = 80 |
|---|---|---|
| Cough | 25 (29.8) | 28 (35.0) |
| Productive Cough** | 21 (25.0) | 10 (12.5) |
| Pharyngolaryngeal Pain | 7 (8.3) | 10 (12.5) |
| Nasal Congestion | 8 (9.5) | 8 (10.0) |
| Pyrexia | 4 (4.8) | 7 (8.8) |
| Crackles Lung | 6 (7.1) | 6 (7.5) |
| Headache | 10 (11.9) | 5 (6.3) |
| Dyspnoea | 8 (9.5) | 5 (6.3) |

TABLE 7-continued

Treatment-Emergent Adverse Events (TEAEs) Reported by ≧5% Patients in Either Treatment Group during the AZLI/placebo Treatment Period

| TEAEs*, n (%) | Placebo n = 84 | AZLI n = 80 |
|---|---|---|
| Wheezing | 7 (8.3) | 5 (6.3) |
| Chest Discomfort | 4 (4.8) | 5 (6.3) |
| Throat Irritation | 2 (2.4) | 5 (6.3) |
| Fatigue | 7 (8.3) | 3 (3.8) |
| Pulmonary Function Test Decreased | 6 (7.1) | 3 (3.8) |
| Abdominal Pain | 6 (7.1) | 2 (2.5) |
| Haemoptysis | 6 (7.1) | 2 (2.5) |

*TEAEs coded using the Medical Dictionary for Regulatory Activities (MedDRA, Version 8.0) preferred term.
**Significantly fewer in AZLI group (P = 0.047), Fisher's Exact Test; tested if TEAE incidence ≧10% in either treatment group.

Clinical Trial III
Study CP-AI-006:

This is an ongoing open-label, multicenter study evaluating the safety and efficacy of repeated AZLI exposure in CF patients who participated in either Clinical Trial I or Clinical Trial II described above. Patients receive up to nine 28-day courses of AI in the same regimen, BID or TID, to which they were assigned in either Clinical Trial I or Clinical Trial II. Each course of AZLI is followed by a 28-day off drug period. Patients must have completed Clinical Trial I or Clinical Trial II or have been withdrawn due to need for antipseudomonal antibiotics or due to an adverse event (AE) unrelated to study medication intolerance. During the study, patients may be treated as needed with any antipseudomonal antibiotics (oral, IV, or inhaled) with the exception of IV aztreonam. At the 1 Mar. 2007 interim data cut-off 207 patients had been enrolled and had at least one post-enrollment visit. There are 82 patients in the AI BID group and 125 in the AI TID group. The safety profile observed over the first three courses was consistent with the expected symptoms of the patients' underlying CF lung disease. Respiratory symptoms were the predominant cause of AE reports. No differences were observed between regimens in the overall rates of AEs, drug-related AEs, or significant adverse events (SAEs). There was little change in susceptibility of PA to aztreonam during the trial. In both the BID and TID treatment groups, the $MIC_{50}$ remained unchanged (±2-fold change) from Visit 1, while transient increases in the $MIC_{90}$ were observed. Following completion of each of the first three courses of AZLI, the absolute mean change from baseline in CFQ-R respiratory symptoms domain scores was greater in the TID group compared to the BID group. Similarly, $FEV_1$ ([L] and % predicted) was improved relative to baseline after each 28-day course of AZLI, with group means returning to baseline at the end of the 28-day follow-up period (prior to the next course of AZLI). The percent change from Visit 1 in $FEV_1$ was higher in the TID than the BID group at the end of each of the first three AZLI courses. The percent change from Visit 1 remained higher in the TID group at Visit 6, compared to the BID group, but was not statistically significant. PA sputum density decreased relative to baseline in both groups during treatment; the decreases were consistently larger among TID-treated than BID-treated patients.

Mean Change in CFQ-R Respiratory Symptoms Domain Scores from Day 0:

In the open-label follow on study, the mean CFQ-R respiratory symptoms domain scores at baseline (Visit 1) were approximately 66 and 62 for the BID and TID groups respectively. Mean (standard deviation (SD)) change in CFQ-R respiratory symptoms domain score after the first 28 days of open-label therapy was 3.53 (12.53) for the BID group and 7.06 (16.35) for the TID group This change is consistent with that observed after 28 days of AZLI therapy in the controlled trials. Table 8 shows change in CFQ-R respiratory symptoms domain scores from Day 0 of the open-label trial to the end of the first three open-label AZLI courses and the last attended visit of the open-label trial.

TABLE 8

Mean Change in CFQ-R Respiratory Symptoms Domain Scores from Day 0 to End of Treatment Courses-Open-label Trial

| | AI BID (N = 82) | AI TID (N = 125) |
|---|---|---|
| End Course 1 (Day 28) | | |
| n | 78 | 124 |
| Mean (SD) | 3.53 (12.53) | 7.06 (16.35) |
| Median | 5.56 | 5.56 |
| Range | −38.9-27.8 | −38.9-72.2 |
| End Course 2 (Day 84) | | |
| n | 75 | 106 |
| Mean (SD) | 2.93 (13.98) | 6.39 (16.46) |
| Median | 0.00 | 5.56 |
| Range | −50.0-33.3 | −38.9-55.6 |
| End Course 3 (Day 140) | | |
| n | 69 | 88 |
| Mean (SD) | −0.16 (19.78) | 7.45 (19.01) |
| Median | 0.00 | 5.56 |
| Range | −61.1-33.3 | −44.4-50.0 |
| Last Attended Visit | | |
| n | 79 | 124 |
| Mean (SD) | 0.84 (16.29) | 4.03 (19.60) |
| Median | 0.00 | 2.78 |
| Range | −61.11-44.44 | −61.11-66.67 |

Figure 9:
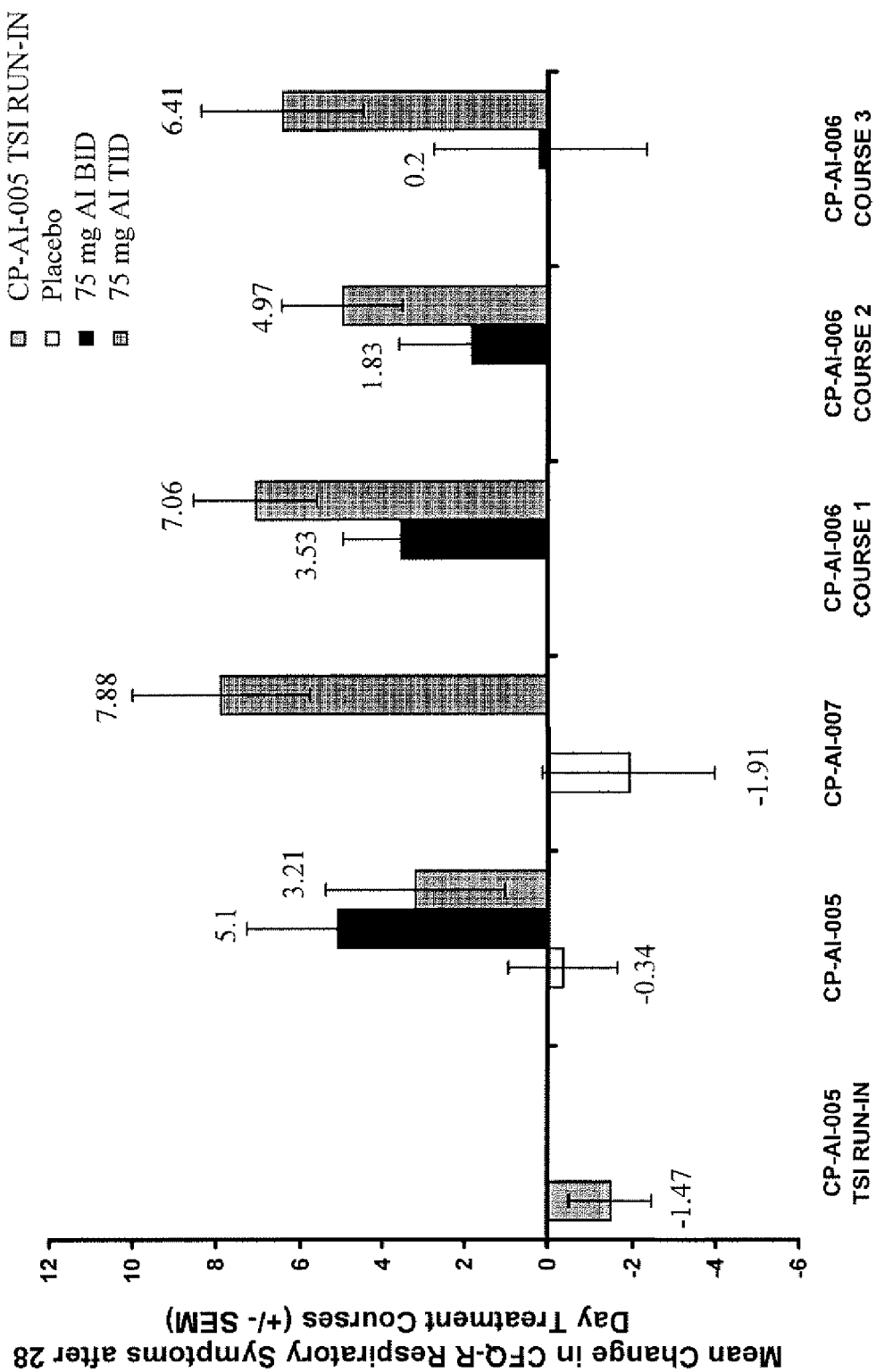
FIG. 9. Change in CFQ-R Respiratory Symptoms Domain Scores during 28 Day AZLI Treatment Courses.

FIG. 9 compares the mean change in CFQ-R respiratory symptoms domain scores observed from baseline to Day 28 in the controlled trials to that observed from the first day to last day of each of the first three AZLI treatment courses (ie, within each 28 day interval) in the open-label trial. Note that the data in FIG. 9 are change within courses and therefore do not match Table 8. The change in mean CFQ-R respiratory symptoms domain scores observed during the TSI run in period of Clinical Trial I are also shown for comparison.

Mean Change in CFQ-R Respiratory Symptoms Domain Scores from Day 0 of Open-Label Follow-on-Trial by Previous Study:

Table 9 shows mean change in CFQ-R respiratory symptoms domain scores from Day 0 of Clinical Trial III by previous study. At the completion of each of the first three open-label AZLI treatment courses, mean changes were greater for patients from Clinical Trial II than for patients from of Clinical Trial I.

TABLE 9

Mean Change in CFQ-R Respiratory Symptoms Domain Scores from Day 0 of Open Label Trial by Previous Trial (Observed Case Data)

|  | Clinical Trial I | | | Clinical Trial II |
| --- | --- | --- | --- | --- |
|  | AI BID (N = 82) | AI TID (N = 74) | AI Pooled (N = 156) | AI TID (N = 51) |
| End Course 1 (Day 28) | | | | |
| n | 78 | 73 | 151 | 51 |
| Mean (SD) | 3.53 (12.54) | 7.61 (15.78) | 5.50 (14.93) | 6.26 (17.26) |
| Median | 5.56 | 5.56 | 5.56 | 5.56 |
| Range | −38.89-27.78 | −33.33-66.67 | −38.89-66.67 | −38.89-72.22 |
| End Course 2 (Day 84) | | | | |
| n | 75 | 67 | 142 | 39 |
| Mean (SD) | 2.93 (13.98) | 4.39 (16.00) | 3.62 (14.93) | 9.83 (16.88) |
| Median | 0.00 | 5.56 | 0.00 | 11.11 |
| Range | −50.00-33.33 | −38.89-55.56 | −50.00-55.56 | −33.33-55.56 |
| End Course 3 (Day 140) | | | | |
| n | 70 | 59 | 129 | 29 |
| Mean (SD) | 0.08 (19.74) | 6.36 (20.56) | 2.95 (20.28) | 9.67 (15.48) |
| Median | 0.00 | 0.00 | 0.00 | 5.56 |
| Range | −61.11-33.33 | −44.44-50.00 | −61.11-50.00 | −22.22-50.00 |

Categorical Change in CFQ-R Respiratory Symptoms Domain Scores:

Table 10 shows the categorical change in CFQ-R respiratory symptoms domain scores over the first three AZLI courses in Clinical Trial III; change is from Day 0 of the open-label trial. At the end of the first three courses, the proportion of patients with improvement in symptoms was approximately 20% greater than the proportion with worsening of symptoms. A greater proportion of patients in the TID than BID group had improved symptoms.

TABLE 10

Categorical Change in CFQ-R Respiratory Symptoms Domain Scores First Three AZLI Courses of Open-label Follow on Trial

|  | AZLI BID (N = 82) n (%) | AZLI TID (N = 125) n (%) | AZLI Total (N = 207) n (%) |
| --- | --- | --- | --- |
| End Course 1 (Day 28) | | | |
| n | 78 | 124 | 202 |
| Improved | 40 (51.3) | 79 (63.7) | 119 (57.5) |
| Stable or no change | 22 (28.2) | 13 (10.5) | 35 (16.9) |
| Worsened | 16 (20.5) | 32 (25.8) | 48 (23.2) |
| End Course 2 (Day 84) | | | |
| n | 75 | 106 | 181 |
| Improved | 33 (44.0) | 61 (57.5) | 94 (51.9) |
| Stable or no change | 22 (29.3) | 21 (19.8) | 43 (23.7) |
| Worsened | 20 (26.7) | 24 (22.6) | 44 (24.3) |
| End Course 3 (Day 140) | | | |
| n | 69 | 88 | 157 |
| Improved | 32 (46.4) | 49 (55.7) | 81 (51.6) |
| Stable or no change | 13 (18.8) | 17 (19.3) | 30 (19.1) |
| Worsened | 24 (34.8) | 22 (25.0) | 46 (29.9) |

Improved - increase in score of ≧5
Stable or no change - change of less than 5 (increase or decrease)
Worsened - decrease in score of ≧5

Open-Label Follow On Trial
Mean Relative Change in $FEV_1$ % Predicted:

Table 11 shows mean relative change in $FEV_1$ % predicted from Day 0 to the end of each of the first three AI treatment intervals of the open-label trial. There was positive $FEV_1$ response noted at the end of each treatment course; a consistently greater response was observed in the TID arm. These results are supportive of those observed during the controlled trials.

TABLE 11

Mean Relative Change in $FEV_1$ % Predicted from Day 0-Open-label Trial

|  | AZLI BID (N = 82) | AZLI TID (N = 125) |
| --- | --- | --- |
| End Course 1 (Day 28) | | |
| n | 80 | 122 |
| Mean (SD) | 4.10 (10.48) | 9.85 (17.27) |
| Median | 3.61 | 6.94 |
| Range | −17.71-36.34 | −25.26-108.86 |
| End Course 2 (Day 84) | | |
| n | 75 | 107 |
| Mean (SD) | 2.40 (8.89) | 8.65 (19.00) |
| Median | 3.18 | 6.02 |
| Range | −16.74-23.86 | −44.08-110.48 |
| End Course 3 (Day 140) | | |
| n | 71 | 90 |
| Mean (SD) | 2.63 (11.47) | 6.86 (18.27) |
| Median | 3.61 | 4.93 |
| Range | −32.24-28.76 | −37.91-93.83 |

Figure 10:
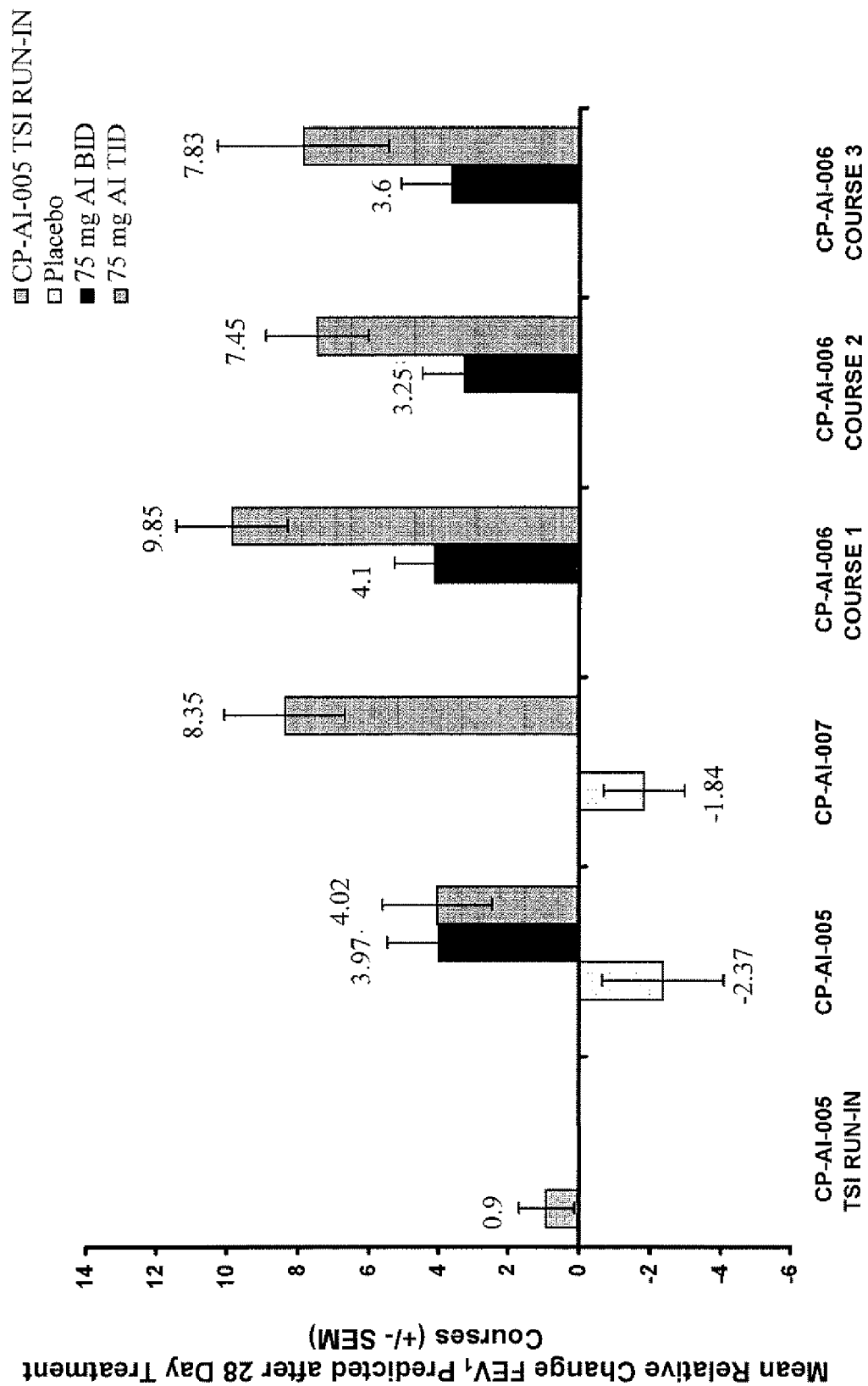
FIG. 10. Mean Relative Change in $FEV_1\%$ Predicted over 28-day AZLI Treatment Courses.

FIG. 10 shows the $FEV_1$ response within each of the first three AZLI treatment courses in the open-label trial. The relative change in $FEV_1$ % predicted observed during the treatment periods of the Phase 3 controlled trials, as well as that for the TSI run in period of Clinical Trial I is presented for comparison.

Mean Percent Change in $FEV_1$ (L):

Table 12 presents results for mean percent change in $FEV_1$ (L). There are no meaningful differences between these results and those for mean relative change in $FEV_1$, % predicted.

TABLE 12

Mean Percent Change in FEV$_1$ (L) from Day 0-Open Label Trial

|  | AZLI BID (N = 82) | AZLI TID (N = 125) |
|---|---|---|
| End Course 1 (Day 28) | | |
| n | 80 | 122 |
| Mean (SD) | 4.05 (10.27) | 9.86 (17.27) |
| Median | 3.71 | 6.99 |
| Range | −17.50-33.33 | −25.13-108.74 |
| End Coarse 2 (Day 84) | | |
| n | 75 | 107 |
| Mean (SD) | 2.43 (8.85) | 8.66 (18.98) |
| Median | 3.50 | 5.48 |
| Range | −16.86-23.68 | −44.16-110.16 |
| End Course 3 (Day 140) | | |
| n | 70 | 97 |
| Mean (SD) | 2.72 (11.51) | 6.76 (18.22) |
| Median | 3.59 | 4.41 |
| Range | −31.74-28.37 | −37.57-93.20 |

Mean Relative Change in FEV$_1$% Predicted by Previous Study:

Table 13 presents mean relative change in FEV$_1$% predicted during the first three courses of the open-label study by previous trial. Positive FEV$_1$ response was observed during each course in patients from both studies; the TID arm had a consistently larger response than the BID arm in Clinical Trial I. Patients from Clinical Trial II had greater improvement in FEV$_1$% predicted during each treatment courses than did patients from either the BID or TID arms of Clinical Trial I.

TABLE 13

Mean Relative Change in FEV$_1$ % Predicted by Previous Study-Open-label Trial

| | Clinical Trial I | | | Clinical Trial II |
|---|---|---|---|---|
| | AZLI BID (N = 82) | AZLI TID (N = 74) | AZLI Pooled (N = 156) | AZLI TID (N = 51) |
| End course 1 (Day 28) | | | | |
| n | 80 | 72 | 152 | 50 |
| Mean (SD) | 4.10 (10.48) | 8.93 (16.18) | 6.39 (13.65) | 11.19 (18.81) |
| Median | 3.61 | 6.55 | 4.99 | 7.92 |
| Range | −17.71-33.34 | −25.26-66.56 | −25.26-66.56 | −13.85-108.86 |
| End course 2 (Day 84) | | | | |
| n | 75 | 67 | 142 | 40 |
| Mean (SD) | 2.40 (8.89) | 5.32 (13.65) | 3.78 (11.44) | 14.23 (24.78) |
| Median | 3.18 | 4.39 | 3.76 | 7.32 |
| Range | −16.74-23.86 | −44.08-47.00 | −44.08-47.00 | −22.11-110.48 |
| End course 3 (Day 140) | | | | |
| n | 71 | 60 | 131 | 30 |
| Mean (SD) | 2.63 (11.47) | 3.54 (15.00) | 3.04 (13.16) | 13.51 (22.32) |
| Median | 3.61 | 2.08 | 3.17 | 7.78 |
| Range | −32.24-28.76 | −37.91-42.22 | −37.91-42.22 | −11.17-93.83 |

Mean Percent Change in FEV$_1$ (L) by Previous Study:

Table 14 presents data for mean percent change in FEV$_1$ (L) by previous study. There are no meaningful differences between these results and those for mean relative change in FEV$_1$% predicted (See Table 13).

TABLE 14

Mean Percent Change in FEV$_1$ (L) by Previous Study-Open Label Trial

| | Clinical Trial I | | | Clinical Trial II |
|---|---|---|---|---|
| | AZLI BID (N = 82) | AZLI TID (N = 74) | AZLI Pooled (N = 156) | AZLI TID N = 51 |
| End Course 1 (Day 28) | | | | |
| n | 80 | 72 | 152 | 50 |
| Mean (SD) | 4.05 (10.27) | 8.93 (16.21) | 6.36 (13.59) | 11.20 (18.78) |
| Median | 3.71 | 6.60 | 4.93 | 7.95 |
| Range | −17.50-33.33 | −25.13-66.47 | −25.13-66.47 | −13.89-108.74 |
| End Course 2 (Day 84) | | | | |
| n | 75 | 67 | 142 | 40 |
| Mean (SD) | 2.43 (8.85) | 5.35 (13.72) | 3.81 (11.46) | 14.22 (24.69) |
| Median | 3.50 | 4.26 | 3.60 | 7.17 |
| Range | −16.86-23.68 | −44.16-48.00 | −44.16-48.00 | −22.11-110.16 |

TABLE 14-continued

Mean Percent Change in FEV$_1$ (L) by Previous Study-Open Label Trial

| | Clinical Trial I | | | Clinical Trial II |
| --- | --- | --- | --- | --- |
| | AZLI BID (N = 82) | AZLI TID (N = 74) | AZLI Pooled (N = 156) | AZLI TID N = 51 |
| End Course 3 (Day 140) | | | | |
| n | 71 | 60 | 131 | 30 |
| Mean (SD) | 2.72 (11.43) | 3.56 (15.04) | 3.11 (13.16) | 13.14 (22.25) |
| Median | 3.33 | 2.26 | 3.00 | 6.21 |
| Range | −31.74-28.37 | −37.57-41.84 | −37.57-41.84 | −11.43-93.20 |

Discussion

The most important efficacy endpoint for the clinical development program, change in CFQ-R respiratory symptoms domain scores, measured patient perception of change in their respiratory symptoms. This endpoint showed a significant difference between AZLI and placebo groups in both studies. At both Days 14 and 28, the treatment differences for Clinical Trial II (7.98 and 9.71) and Clinical Trial I (5.53 and 5.01) demonstrated a clinically significant improvement in respiratory symptoms among AZLI treated patients compared to placebo; this improvement persisted through Day 42 in study Clinical Trial II. A change of five points represents the minimum change that can be detected by an individual patient. Furthermore, significantly greater percentages of patients receiving AZLI compared to placebo had scores indicating improvement in respiratory symptoms, and a lower percentage had worsening symptoms at Days 14 and 28. Similar results have been observed in the ongoing open label trial, with larger change scores for patients who rolled over from Clinical Trial II; some attenuation of response is observed in the second and third AZLI courses among patients from study Clinical Trial I; but an analysis of the combined trials shows a sustained response. Among AZLI treated patients, increases in CFQ-R respiratory symptoms domain scores were greater among patients with baseline FEV$_1$>50% predicted, females, and those from outside the US. The finding that females had greater improvement in CFQ-R scores was not unexpected. Gender differences have been well documented in CF patients, with females historically having poorer outcomes, but stronger response to therapy, as demonstrated in the TSI registration trials.

Consistent with the observed improvement in respiratory symptoms and reduction in antibiotic use, two key markers traditionally used to evaluate the efficacy of antibiotic therapies in CF, change in pulmonary function and PA density in sputum, demonstrated a significant advantage for AZLI treated patients. By Day 14 of AZLI treatment in both controlled trials, FEV$_1$ ([L] and % predicted) had improved significantly compared to placebo. At Day 28, the treatment differences between the AZLI and placebo groups for mean percent change in FEV$_1$ (L) were 6.3% (Clinical Trial I) and 10.3% (Clinical Trial II), respectively; the difference between groups for relative change in FEV$_1$% predicted were 6.6% and 10.2%. These results compare favorably with the treatment effect observed in the registration trials for TSI and Pulmozyme, as well as a European trial comparing inhaled tobramycin and colistin (See Table 15). Moreover, these improvements were maintained through Day 42, 14 days after the end of AZLI treatment, whereas FEV$_1$ response in the TSI trials peaked at Day 14 and declined thereafter. The treatment effect in Clinical Trial I is noteworthy in that these patients had received a 28 day TSI course immediately prior to AZLI therapy; the minimal improvement (0.9%) observed during the TSI run in period would not predict that a robust increase in pulmonary function could be achieved within 14 days of AZLI therapy.

FEV$_1$ response in the first three courses of the open label trial show consistent improvements over baseline. As observed for the change in patient perception of symptoms, patients who rolled over from Clinical Trial II had more pronounced FEV$_1$, response in the open label trial; by the end of the third course (6 months after beginning open label treatment), improvement in FEV$_1$% predicted (13.5%) was greater than after the end of the first course (12.0%); and the open label results for patients from Clinical Trial III contrasted sharply with the negligible change in FEV$_1$% predicted observed during the TSI run in phase of Clinical Trial I (0.9%). This is also greater than the improvement observed at the end of the third TSI course (10%) of the TSI registration trials.

Greater improvements in FEV$_1$ were observed for patients with less severe baseline disease and more susceptible PA isolates, as well as those from outside the US. The finding of comparable FEV$_1$ response for AZLI treated patients of all age groups differ from the TSI registration trial results where response among patients 13 to 17 years was significantly greater than among younger or older patients.

Reduction in PA CFU density mirrored increases in pulmonary function during the 28 day treatment course, with significant decreases for AZLI treated patients in both studies observed within 14 days of the start of treatment. At Day 14, the treatment differences for Clinical Trial I and Clinical Trial II were 0.49 and 0.88 log$_{10}$, respectively, by Day 28 the treatment differences between groups increased to 0.66 log$_{10}$ and 1.45 log$_{10}$. The magnitude of these reductions is comparable to those observed in studies of inhaled tobramycin and colistin, including the TSI registration trials (See Table 15). Following cessation of treatment, CFU density increased and by Day 42, although respiratory symptoms and pulmonary function still showed improvement over baseline for AZLI treated patients, CFU density was near, or exceeded, baseline values. In the open label follow on trial, CPU density decreased during each of the first three 28 day courses, but the magnitude of the reductions was not as great as at Day 28 of treatment in the controlled trials. These results are consistent with those from the TSI registration trials, where there was a reduced effect in later treatment courses. The smaller reduction observed between days 0 and 28 in Clinical Trial I may be attributed to the TSI treatment during the run in phase, as prior antibiotic treatment may attenuate CFU response. Reductions in CFU density were larger for AZLI treated patients with less severe disease, more susceptible PA isolates, males and patients under 18 years of age; this latter result is consistent with the TSI trials which showed decreased CPU response with increasing age.

TABLE 15

Relative Change in FEV₁ from Baseline in Previous Studies

| Study | Pulmonary Function Entry Criteria[a] | Baseline FEV₁ % Predicted (mean ± SD)[a] | Dose (mg)/ Duration | FEV₁ Change | PA Density Change ($Log_{10}$) |
|---|---|---|---|---|---|
| Tobramycin[21] (N = 36) | FVC > 40% | 55 ± 3.7 to 60 ± 3.2 | 600 TID | 10%[a] | −2.0 |
| TOBI (All) (N = 258)[1] | FEV₁ 25-75% | 49.9 + 15.5 | 300 BID/28 days | 12%[b] | −2.0 |
| Adolescents (N = 63)[1] | FEV₁ 25-75% | unk | 300 BID/28 days | ~16%[b] | not evaluated |
| Adults (N = 140)[1] | FEV₁ 25-75% | unk | 300 BID/28 days | ~6%[b] | not evaluated |
| TOBI (N = 53) | FEV₁ ≧ 25% | 55.4 + 22.9 | 300 BID/28 days | 7%[b] | −0.9 |
| Colistin[20] (N = 62) | FEV₁ ≧ 25% | 59.4 ± 22.6 | 80 BID/28 days | 0%[b] | −0.6 |
| Pulmozyme[19] | FVC > 40% | 61.1 ± 26.9 | 2.5 mg BID/24 weeks | 5.8 ± 0.7[c] | not evaluated |
| Pulmozyme[19] | FVC > 40% | 60.0 ± 2.69 | 2.5 mg TID/24 weeks | 5.6 ± 0.7[c] | not evaluated |

[a]Absolute change in FEV₁ % predicted, comparison to control after 28 days of therapy
[b]Relative change in FEV₁ % predicted, comparison to control after 28 days of therapy
[c]Percent change in FEV₁ (L), comparison to control after 24 weeks of therapy
[d]FEV₁ change is relative change compared to control at 28 days In addition to showing improvement in respiratory symptoms, the CFQ-R demonstrated improvements in non-respiratory domains of physical functioning, emotional functioning, body image, eating disturbances, role limitations/school performance, weight disturbances, vitality, and treatment burden. These results have particular relevance for patients with a chronic illness, who must adhere to complex, time-consuming medical regimens that affect their normal activities. Their perception of treatment benefit is likely to improve adherence to treatment regimens and influence their long-term health outcomes.

Increases in weight and body mass index in patients treated with AZLI vs. placebo provided additional confirmation of the general health benefit derived from AZLI therapy during these trials.

It is important to note that therapeutic benefit was demonstrated in all subgroups defined by age, baseline disease severity and PA susceptibility, and gender and that similar results were obtained from three trials which can be viewed as bracketing the current standard of care for CF lung disease (i.e. Clinical Trial II=therapy in patients off antibiotics for 28+ days, Clinical Trial I=therapy in extensively treated patients immediately following a 28 day TSI course, and Clinical Trial III=therapy in patients currently treated as clinically indicated).

The above embodiments represent certain aspects of the invention. Additional objects, aspects and embodiments would be apparent to one skilled in the art and are intended to be encompassed by the instant invention.

All references cited in the instant application are incorporated by reference herein in their entirety.

What is claimed:

1. A method of improving a health-related quality-of-life score in a patient having cystic fibrosis comprising administering a therapeutically effective amount of an inhalable dry powder or aerosol comprising about 1 to about 250 mg of aztreonam lysine per one dose to the airways of the patient's lung using a dosing regimen comprising administering said inhalable dry powder or aerosol for at least 14 to 28 consecutive days followed by a drug holiday of at least 14 to 28 consecutive days and repeating the dosing regimen for two, three, four, five, six, seven, eight, or nine courses.

2. The method of claim 1 wherein one dose of inhalable dry powder or aerosol is administered 2 to 10 times a day.

3. The method of claim 1 wherein said cystic fibrosis patient has a pulmonary *Pseudomonas aeruginosa* infection.

4. The method of claim 1 wherein the health-related quality-of-life score is measured by one, two, three, four, five, six, seven, eight, nine, ten, eleven or all of the symptom domains of the Cystic Fibrosis Questionnaire-Revised.

5. The method of claim 4 wherein the symptom domain is selected from the group consisting of the respiratory domain, the body image domain, the digestion domain, the eating domain, the emotional domain, the health perceptions domain, the physical domain, the role/school domain, the social domain, the treatment burden domain, the vitality domain, and the weight domain.

6. The method of claim 5 wherein the symptom domain is the respiratory domain.

7. The method of claim 5 wherein one dose of the inhalable aerosol is dissolved in about 1 to about 5 mL of a saline solution comprising about 0.1 to about 0.45%, w/v, of sodium chloride.

8. The method of claim 7 wherein the inhalable aerosol is delivered by an electronic nebulizer adapted to deliver predominantly aerosol particle sizes comprising mass median aerodynamic diameters of about 1 to about 5μ.

9. The method of claim 8 wherein the dose of inhalable aerosol is administered three times a day.

10. The method of claim 9 wherein at least one of the symptom domain scores is increased by at least 5 points compared to the scores immediately before beginning the dosing regimen.

11. The method of claim 9 wherein each dose of inhalable aerosol comprises about 75 mg of aztreonam dissolved in about 1 mL of saline comprising about 0.17%, w/v, sodium chloride.

12. The method of claim 11 wherein the respiratory domain score is increased by at least 5 points compared to the score immediately before beginning the dosing regimen.

13. The method of claim 3 wherein the dosing regimen is preceded by a standard prescribed 28-day administration of tobramycin inhalation solution.

14. The method of claim 13 wherein the dosing regimen comprising administering said inhalable dry powder or aerosol for 28 consecutive days followed by a 28-day drug holiday.

* * * * *